(12) United States Patent
Patterson et al.

(10) Patent No.: US 8,214,227 B2
(45) Date of Patent: *Jul. 3, 2012

(54) OPTIMIZED PRACTICE PROCESS MODEL FOR CLINICAL PROCESS IMPROVEMENT

(75) Inventors: Neal L. Patterson, Belton, MO (US); Paul N. Gorup, Parkville, MO (US)

(73) Assignee: Cerner Innovation, Inc., Overland Park, KS (US)

(*) Notice: Subject to any disclaimer, the term of this patent is extended or adjusted under 35 U.S.C. 154(b) by 958 days.

This patent is subject to a terminal disclaimer.

(21) Appl. No.: 11/278,084

(22) Filed: Mar. 30, 2006

(65) Prior Publication Data

US 2007/0083385 A1 Apr. 12, 2007

Related U.S. Application Data

(60) Provisional application No. 60/724,982, filed on Oct. 7, 2005.

(51) Int. Cl.
*G06Q 50/00* (2012.01)

(52) U.S. Cl. ......... 705/2; 705/7.38; 705/7.39; 705/7.41; 705/3; 600/300

(58) Field of Classification Search .............. 705/2, 3, 705/4
See application file for complete search history.

(56) References Cited

U.S. PATENT DOCUMENTS

| | | | | |
|---|---|---|---|---|
| 5,778,345 | A * | 7/1998 | McCartney | 705/2 |
| 6,230,142 | B1 * | 5/2001 | Benigno et al. | 705/3 |
| 6,782,372 | B1 | 8/2004 | Cooper | |
| 2001/0032195 | A1 * | 10/2001 | Graichen et al. | 705/400 |
| 2002/0107819 | A1 | 8/2002 | Ouimet | |
| 2003/0149586 | A1 | 8/2003 | Chen | |
| 2003/0216939 | A1 * | 11/2003 | Bito et al. | 705/2 |
| 2004/0093244 | A1 | 5/2004 | Hatcher | |
| 2004/0143462 | A1 * | 7/2004 | Hunt et al. | 705/3 |
| 2004/0176980 | A1 * | 9/2004 | Bulitta et al. | 705/2 |
| 2004/0224296 | A1 * | 11/2004 | Carraccio | 434/322 |
| 2005/0038669 | A1 * | 2/2005 | Sachdeva et al. | 705/2 |
| 2005/0182657 | A1 | 8/2005 | Abraham-Fuchs et al. | |

OTHER PUBLICATIONS

Non Final Office Action of U.S. Appl. No. 11/278,085, mailed Feb. 2, 2010.
Final Office Action of U.S. Appl. No. 11/278,085, mailed Jul. 1, 2010.

* cited by examiner

*Primary Examiner* — R. David Rines
(74) *Attorney, Agent, or Firm* — Shook Hardy & Bacon LLP

(57) ABSTRACT

Systems, methods, and graphical user interfaces are provided for identifying, analyzing, and adopting opportunities for optimizing clinical processes within clinical facilities. An optimized practice process model may be defined for a particular clinical procedure, setting forth an optimal clinical process. In addition, critical levers may be identified within the optimal clinical process, representing the activities that have the greatest impact on outcomes. Clinical facilities may collect current measures for the critical levers, and the current measures may be compared against an optimal, benchmark, and/or target measure. Based on the comparison, opportunities for clinical process optimization may be identified. Those opportunities may then be analyzed and prioritized for adoption into a facility's current practice. Clinical processes within healthcare facilities may be further improved by continuously monitoring facility data and identifying further opportunities of optimization. Further, collected data may be used to refine the optimized practice process model, allowing for further optimization.

3 Claims, 20 Drawing Sheets

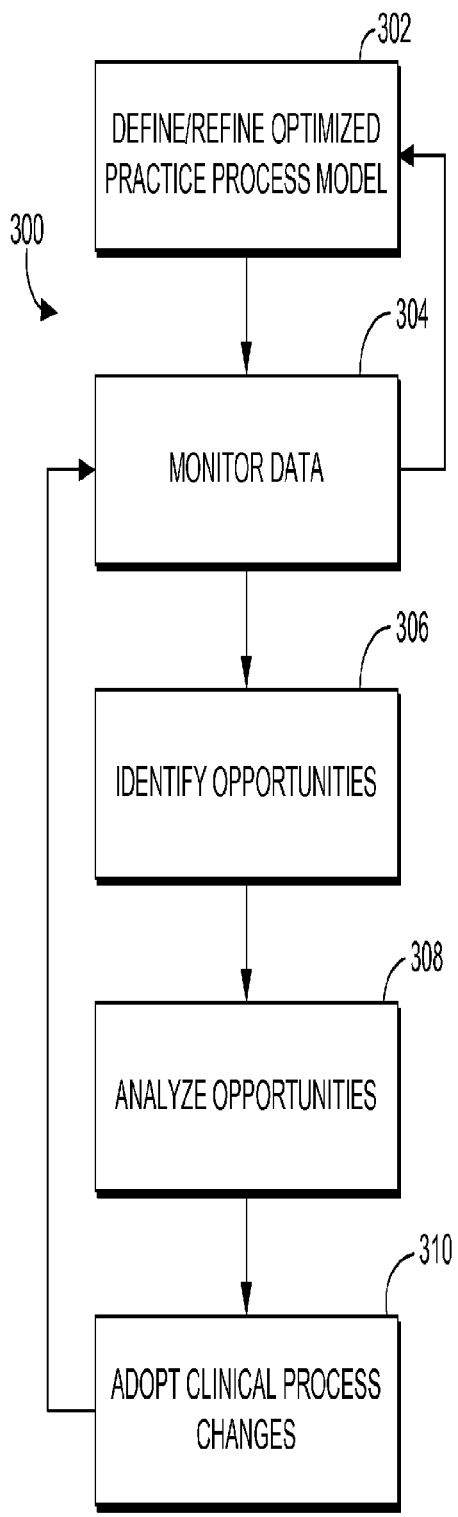
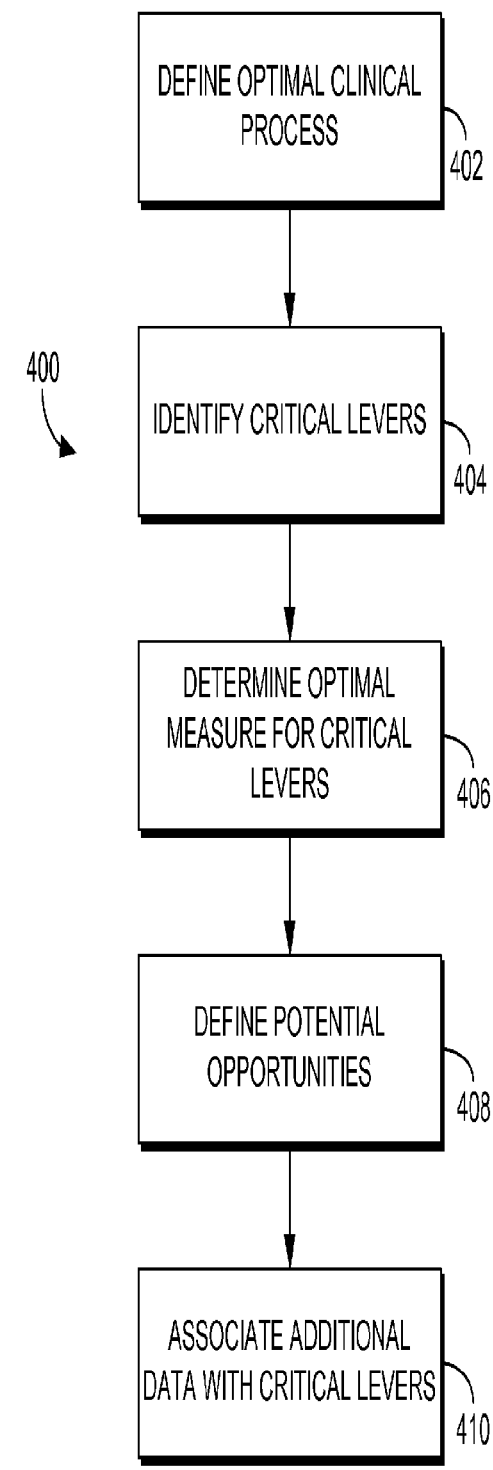
FIG. 3.
FIG. 4.

| 602 AREA OF ANALYSIS | 604 VENUE | | | | | |
|---|---|---|---|---|---|---|
| | AMBULATORY | ED | PERIOPERATIVE | CRITICAL CARE | ACUTE CARE | POST ACUTE CARE |
| QUALITY CARE | | | | | ⬡ | |
| SAFETY/RISK MANAGEMENT | ⬡ (616) | | ⬡ | | ⬡ | |
| COMPLICATION/COMORBIDITY | ? | | | | ⬡ | |
| OPERATIONAL EFFICIENCY | | | ⬡ | | ⬡ | |
| ACCESS MANAGEMENT | ⬡ | | ⬡ | | | |
| RESOURCE MANAGEMENT | ⬡ | | ⬡ | | ◇ | |
| REVENUE CYCLE | ⬡ | | ⬡ | | ⬡ | |

606 ⬡ - AREA OF OPPORTUNITY
608 ◇ - AREA OF POSSIBLE OPPORTUNITY
610 ○ - CLIENT IS MEETING THE MEASURE – NO NEED FOR FURTHER INTERVENTION.
612 [?] - NOT ENOUGH INFORMATION.

614:
| DRG | 209 |
| ICD-9 CM | 81.54 |
| TIME PERIOD | 01/01/2005 TO 06/30/2005 |
| STUDY GROUP VOLUME | 336 |

| AREAS OF ANALYSIS | VENUE | | | | | | TOTAL |
|---|---|---|---|---|---|---|---|
| | AMBULATORY | ED | PERIOPERATIVE | CRITICAL CARE | ACUTE CARE | POST ACUTE CARE | |
| QUALITY CARE | | | | | $4,399 | | $4,399 |
| SAFETY/RISK MANAGEMENT | $626 | | $158 | | $13,065 | | $13,849 |
| COMPLICATION/COMORBIDITY | ? | | | | $24,549 | | $24,549 |
| OPERATIONAL EFFICIENCY | | | $52,819 | | $0 | | $52,819 |
| ACCESS MANAGEMENT | $529,890 | | $0 | | | | $529,890 |
| RESOURCE MANAGEMENT | $61,320 | | $135,575 | | $52,335 | | $249,230 |
| REVENUE CYCLE | $0 | | $0 | | $26,450 | | $26,450 |
| TOTALS | $591,836 | | $188,552 | | $120,798 | | $901,186 |

$ = ANNUALIZED BENEFIT

FIG. 7.

| OPPORTUNITY | | 902 | 904 | 906 | EFFORT INDEX | 908 |
|---|---|---|---|---|---|---|
| | ACTIVITY | CLINICAL | REGULATORY | OPERATIONAL | FINANCIAL | |
| HB MANAGEMENT | | | | | 6.0 | |
| | 2.15.6.1.16 CONSIDER TYPE & SCREEN | ✓ | | ✓ | ✓ | |
| | 2.4.8.3.5 INITIATE IRON REPLACEMENT THERAPY | ✓ | | ✓ | ✓ | |
| INFECTION PREVENTION | | | | | 6.0 | |
| | 2.15.6.1.14 CONSIDER ASPIRIN FOR DVT PROPHYLAXIS | ✓ | | | ✓ | |
| | 2.15.7.4.13 CONSIDER PROPHYLAXIS CHOICE | | | | | |
| MEDICAL CLEARANCE | | | | | 10.0 | |
| | 2.15.7 CONDUCT ORTHO PRE ADMISSION TESTING EVALUATION | | | | | |
| | 2.15.7.4.11 CONSIDER ORDER BETA BLOCKER | | | | | |

FACILITY A – ORTHOPEDICS – TKA – SAFETY/RISK MANAGEMENT - AMBULATORY ......SWITCH TO OTHER OPPORTUNITY......

FIG. 9.

| | CLIENT NAME | FACILITY | SERVICE LINE | AREA OF ANALYSIS | INDICATOR | PREVIOUS INDICATOR | DATE CHANGED | STATUS |
|---|---|---|---|---|---|---|---|---|
| ACTION LIST | | | | | | | | |
| | AJRO_WI | KENOSHA | CARDIOLOGY | QUALITY CARE | ○ | ○ | 05/17/05 | NEW |
| | AJRO_WI | TWO RIVERS | CARDIO SURGERY | OPERATIONAL EFFICIENCY | ○ | ○ | 05/18/05 | RESEARCHING |
| | SAMT_AZ | BAYWOOD | ORTHO | QUALITY CARE | ○ | ▽ | 05/17/05 | NEW |
| | SAMT_AZ | BAYWOOD | ORTHO | SAFETY / RISK MANAGEMENT | ○ | ○ | 05/12/05 | RESEARCHING |
| | SAMT_AZ | ESTRELLA | CARDIOLOGY | PATIENT FLOW / THROUGHPUT | ○ | ▽ | 05/18/05 | CHANGES PENDING |
| | SJHS_OK | TULSA | ORTHO | QUALITY CARE | ○ | ▽ | 05/12/05 | RESEARCHING |
| WATCH LIST | | | | | | | | |
| | AJRO_WI | HARTFORD | NEPHROLOGY | PATIENT FLOW / THROUGHPUT | ▽ | ○ | 05/13/05 | RESEARCHING |
| | AJRO_WI | KENOSHA | CARDIOLOGY | QUALITY CARE | ▽ | ○ | 05/17/05 | NEW |
| | SAMT_AZ | BAYWOOD | NEPHROLOGY | QUALITY CARE | ▽ | ▽ | 05/17/05 | NEW |
| | SAMT_AZ | BCSMC | ORTHO | OPERATIONAL EFFICIENCY | ▽ | ▽ | 05/12/05 | CHANGES PENDING |
| | SAMT_AZ | BCSMC | CARDIO SURGERY | OPERATIONAL EFFICIENCY | ▽ | ▽ | 05/18/05 | CHANGES PENDING |
| IMPROVEMENT LIST | | | | | | | | |
| | SJHS_OK | TULSA | ORTHO | SAFETY / RISK MANAGEMENT | ○ | ○ | 05/18/05 | CLEARED |
| | SJHSD_OK | TULSA | ORTHO | PATIENT FLOW / THROUGHPUT | ○ | ▽ | 05/12/05 | CLEARED |
| | SAMT_AZ | ESTRELLA | CARDIOLOGY | QUALITY CARE | ○ | ▽ | 05/12/05 | CLEARED |
| | SAMT_AZ | BAYWOOD | CARDIO SURGERY | SAFETY / RISK MANAGEMENT | ○ | ▽ | 05/17/05 | NEW |

| SAFETY/RISK MANAGEMENT - AMBULATORY | ...SWITCH TO OTHER OPPORTUNITY... ▽ | | | | | |
|---|---|---|---|---|---|---|
| OPPORTUNITY | | | | | | |
| ACTIVITY | MEASUREMENT | BASELINE MEASURE | CURRENT MEASURE | BENCHMARK | OPTIMAL PRACTICE | TARGET |
| HB MANAGEMENT | ACTUAL BENEFIT = $0 | | | | | |
| 2.15.6.1.16 CONSIDER TYPE & SCREEN | % PATIENTS WITH BLOOD TYPE AND SCREEN | 46% | 46% | 100% | 100% | 100% |
| 2.4.8.3.5 INITIATE IRON REPLACEMENT THERAPY | %PATIENTS WITH BASELINE PRE-OP HB OPTIMIZATION >12 G/DL | | | 98% | 98% | |
| INFECTION PREVENTION | ACTUAL BENEFIT = $0 | | | | | |
| 2.15.7.4.13 CONSIDER PROPHYLAXIS CHOICE | % PATIENTS WITH APPROPRIATE PROPHYLACTIC ANTIBIOTIC SELECTION | 67% | 67% | 100% | 100% | 100% |
| MEDICAL CLEARANCE | ACTUAL BENEFIT = $2,500 | | | | | |
| 2.15.7 CONDUCT ORTHO PRE ADMISSION TESTING EVALUATION | % OF TKA CASES CANCELLED WITHIN 24 HOURS OF OR DATE | 7.5% | 5% | 3.8% | 0% | 3.8% |
| | % PATIENTS WITH A BLEEDING TIME ORDER | 91% | 91% | 0% | 0% | 0% |
| 2.15.7.4.1' CONSIDER ORDER BETA BLOCKER | % APPROPRIATE BETA BLOCKER PROPHYLAXIS FOR CARDIOVASCULAR DISEASE | | | 100% | 100% | |

FIG. 21.

OPTIMIZED PRACTICE PROCESS MODEL FOR CLINICAL PROCESS IMPROVEMENT

CROSS-REFERENCE TO RELATED APPLICATIONS

This application claims the benefit of U.S. Provisional Application No. 60/724,982, filed Oct. 7, 2005. Additionally, this application is related by subject matter to the inventions disclosed in the following commonly assigned applications: U.S. application Ser. No. 11/278,085, filed on even date herewith; U.S. application Ser. No. 11/278,087, filed on even date herewith; U.S. application Ser. No. 11/278,089, filed on even date herewith; U.S. application Ser. No. 11/278,090, filed on even date herewith; U.S. application Ser. No. 11/278,092, filed on even date herewith; and U.S. application Ser. No. 11/278,094, filed on even date herewith. Each of the aforementioned applications is herein incorporated by reference in its entirety.

STATEMENT REGARDING FEDERALLY SPONSORED RESEARCH OR DEVELOPMENT

Not Applicable.

BACKGROUND

Patient treatment from the initial diagnosis until the final patient discharge may often involve very complex and involved clinical processes. The clinical process for a particular type of treatment may include hundreds of different activities that are performed by a wide variety of actors within the healthcare environment. Because of the complexity of some clinical processes, there are often many opportunities for optimization to improve the quality, delivery, and cost of healthcare. However, the complexity of clinical processes also often makes it difficult to identify the opportunities that will have the greatest impact on improving the outcomes of the processes in an efficient manner.

A number of different approaches have been taken in an attempt to improve clinical processes within healthcare facilities. For instance, one such approach is transformational consulting. Under this approach, consultants evaluate a clinical facility's current practice for a particular clinical process. The consultants then attempt to identify areas within the facility's current clinical process that require improvement. Based on those identifications, the consultants then attempt to develop changes to the clinical process that may be implemented to improve the process. This may often involve working with the client to determine "on the fly" what changes are appropriate to address the shortcomings of the current clinical process. However, this consulting process is an inefficient approach that is time consuming and labor intensive. Moreover, this approach focuses primarily on the facility's current clinical process, potentially ignoring many opportunities for improvement.

Management information systems have also played a role in attempts to improve clinical processes. These systems allow healthcare personnel to collect, track, and analyze a wide variety of clinical data from healthcare facilities. While the collection and analysis of such data may be helpful, there are a number of limitations to the flexibility and sophistication of current clinical management systems. For example, although management information systems allow healthcare facilities to gather a wide range of data, some systems may not permit modeling or simulation of the effect of proposed changes to current clinical procedures. Other systems that do permit a user to predict or simulate outcomes from process changes may do so based only on the internally generated clinical data sets that are unconstrained by other objective guidelines.

To address the shortcomings of many management information systems, evidence-based modeling of clinical operations has been proposed. Under this approach, effects on outcomes may be evaluated by comparing empirical data accessed from clinical facilities to objective guidelines or criteria. However, this approach also poses a number of limitations. For instance, the objective guidelines or criteria used are merely individual pieces of information that are independent of an entire clinical process. Accordingly, such an approach may fail to account for a change's effect on the entire clinical process, such as any impact to other activities within the process. Further, such systems do not readily provide the ability to efficiently analyze and prioritize clinical process improvements.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to systems, methods, and graphical user interfaces that provide a comprehensive and adaptive approach to optimizing current clinical processes within clinical facilities based on optimized practice process models. The types and aspects of clinical processes that may be optimized using embodiments of the present invention are not limited to treatment aspects but may also address financial, administrative, and operational aspects of healthcare processes. In embodiments, an optimized practice process model may be defined for a particular type of clinical process. The optimized practice process model may comprise a variety of information to aid in the identification of opportunities for improving a current clinical process within a clinical facility. In particular, the optimized practice process model comprises an optimal process flow defined for the type of clinical process, detailing the end-to-end activities for the clinical process. In addition, activities within the optimal process flow that have the greatest potential to impact outcomes are identified as critical levers, and an optimal measure is defined for each critical lever. Each critical lever or a set of critical levers may represent a potential opportunity for improving a current clinical process within a clinical facility. Those potential opportunities may be characterized as clinical, financial, operational, and/or regulatory opportunities. Data for quantifying the benefit and effort for adopting each opportunity may also be associated with each optimized practice process model, allowing for the analysis of the various opportunities for process optimization. Further, because the optimized practice process model details the process flow, data is readily available to aid in determining and adopting the necessary changes to facilities' current clinical processes.

In operation, current measures for clinical activities corresponding with the critical levers identified within an optimized practice process model may be collected from a current clinical process within a clinical facility. The current measures may then be compared against optimal measures, benchmark measures, and/or target measures to identify which areas of potential opportunity defined by the optimized practice process model present areas of opportunity to improve the current clinical process within the clinical facility. The identified opportunities may then be analyzed and prioritized such that the opportunities having the greatest benefit with the least effort may be adopted by the clinical facility first. Those opportunities determined to have the highest priority may then be adopted and integrated into the facility's process.

Embodiments of the present invention further provide a closed-looped process as a facility's clinical process may be continuously monitored to identify out-of-tolerance conditions as well as to identify and prioritize further opportunities for improvement. Moreover, the aggregation of data from multiple facilities allows for refinements to be made to the optimized practice process model based on the wide collection of empirical data.

Accordingly, in one aspect, an embodiment of the present invention is directed to a method, implemented at least in part in a clinical computing environment, for facilitating the improvement of a current clinical process within one or more clinical facilities. The method includes defining an optimized practice process model for a type of clinical process corresponding with the current clinical process, the optimized practice process model defining an optimal clinical process flow for the type of clinical process. The method also includes accessing clinically-related data related to the current clinical process within the clinical facility. The method further includes identifying one or more opportunities for improving the current clinical process based on the optimized practice process model and the clinically-related data. The method still further includes generating one or more user interfaces for analyzing the opportunities.

In another aspect of the invention, an embodiment is directed to a method for defining an optimized practice process model for facilitating improvement of a current clinical process within one or more clinical facilities. The method includes defining a process flow for a type of clinical process corresponding with the current clinical process, the process flow including a plurality of clinical activities. The method also includes identifying one or more critical levers within the plurality of clinical activities. The method further includes determining an optimal measure for each of the one or more critical levers.

In a further aspect, an embodiment is directed to one or more computer-readable media having stored thereon a data structure for facilitating the analysis of a current clinical process within one or more clinical facilities. The data structure includes a first data field containing data representing a critical lever within an optimal clinical process for a type of clinical process corresponding with the current clinical process. The data structure also includes a second data field containing data representing an optimal measure for the critical lever.

BRIEF DESCRIPTION OF THE SEVERAL VIEWS OF THE DRAWINGS

The present invention is described in detail below with reference to the attached drawing figures, wherein:

FIG. 3 is a flow diagram showing an overall method for clinical process optimization in accordance with an embodiment of the present invention;

FIG. 4 is a flow diagram showing a method for defining an optimized clinical practice process model in accordance with an embodiment of the present invention;

FIG. 6 is an illustrative screen display of an exemplary opportunity summary user interface showing opportunities identified by the knowledge manager in accordance with an embodiment of the present invention;

FIG. 7 is an illustrative screen display of an exemplary financial benefits summary user interface showing the financial benefit for identified opportunities in accordance with an embodiment of the present invention;

FIG. 9 is an illustrative screen display of an exemplary opportunity value user interface displaying whether activities provide a clinical, financial, operational, and/or regulatory opportunity in accordance with an embodiment of the present invention;

FIG. 13 is an illustrative screen display of an exemplary net change user interface for viewing monitoring data in accordance with an embodiment of the present invention;

FIG. 14 is an illustrative screen display of an exemplary problem summary user interface in accordance with an embodiment of the present invention;

FIG. 21 is an illustrative screen display showing performance improvements for a selected area of a clinical process in accordance with an embodiment of the present invention.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention provide computerized methods, systems, and graphical user interfaces for identifying, analyzing, and adopting opportunities for optimizing clinical processes based on optimized practice process models. Having briefly provided an overview of the present invention, embodiments of the invention will be discussed with reference to FIGS. 1-21.

Figure 1:
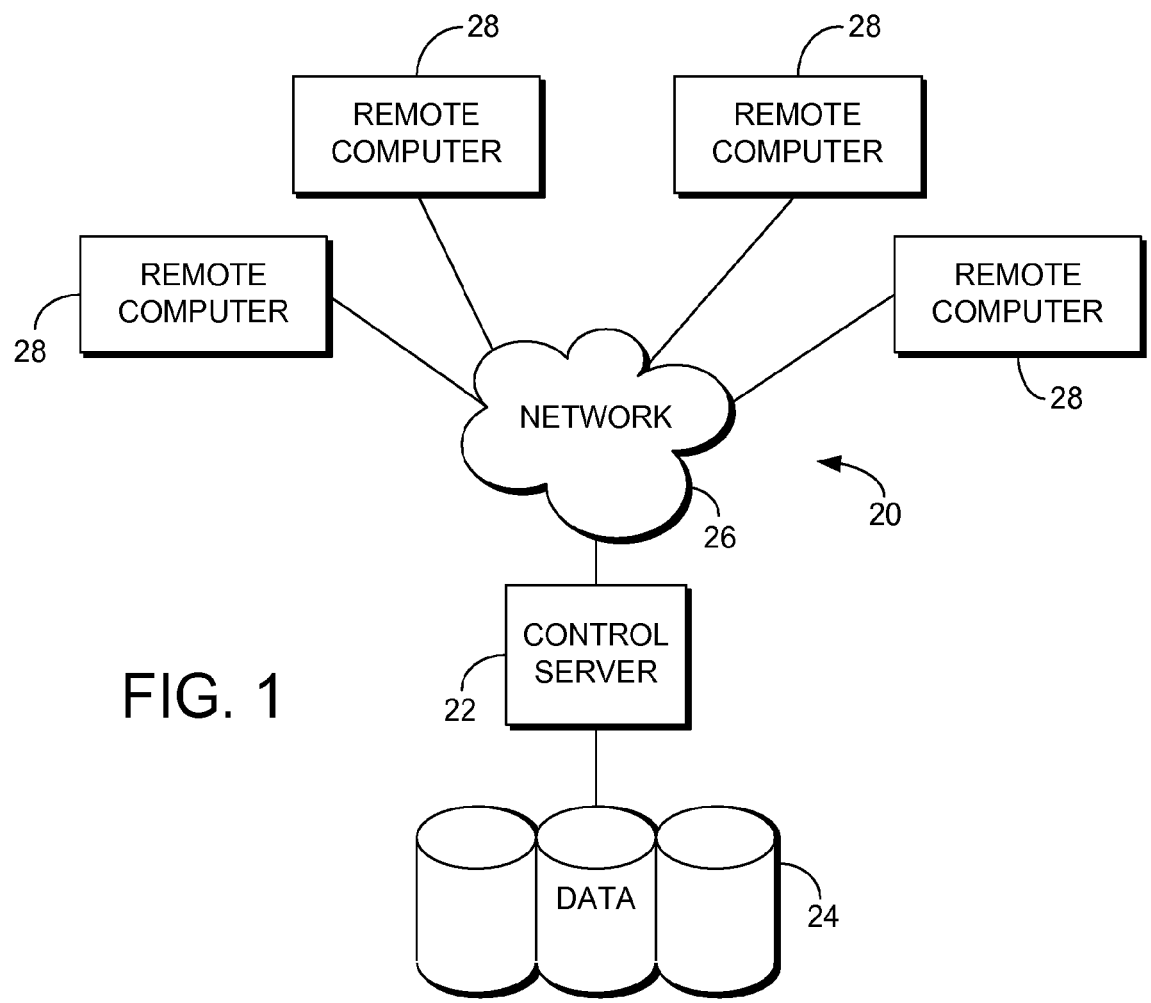
FIG. 1 is a block diagram of an exemplary computing environment suitable for use in implementing the present invention.

Referring to the drawings in general, and initially to FIG. 1 in particular, an exemplary computing system environment, for instance, a medical information computing system, on which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 20 includes a general purpose computing device in the form of a server 22. Components of the server 22 may include, without limitation, a processing unit, internal system memory, and a suitable system bus for coupling various system components, including database cluster 24, with the server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 22 typically includes, or has access to, a variety of computer readable media, for instance, database cluster 24. Computer readable media can be any available media that may be accessed by server 22, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 22. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 24, provide storage of computer readable instructions, data structures, program modules, and other data for the server 22.

The server 22 may operate in a computer network 26 using logical connections to one or more remote computers 28. Remote computers 28 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the components described above in relation to the server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the server 22 may include a modem or other means for establishing communications over the WAN, such as the Internet. In a networked environment, program modules or portions thereof may be stored in the server 22, in the database cluster 24, or on any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., server 22 and remote computers 28) may be utilized.

In operation, a user may enter commands and information into the server 22 or convey the commands and information to the server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 22. In addition to a monitor, the server 22 and/or remote computers 28 may include other peripheral output devices, such as speakers and a printer.

Although many other internal components of the server 22 and the remote computers 28 are not shown, those of ordinary skill in the art will appreciate that such components and their interconnection are well known. Accordingly, additional details concerning the internal construction of the server 22 and the remote computers 28 are not further disclosed herein.

Figure 2:
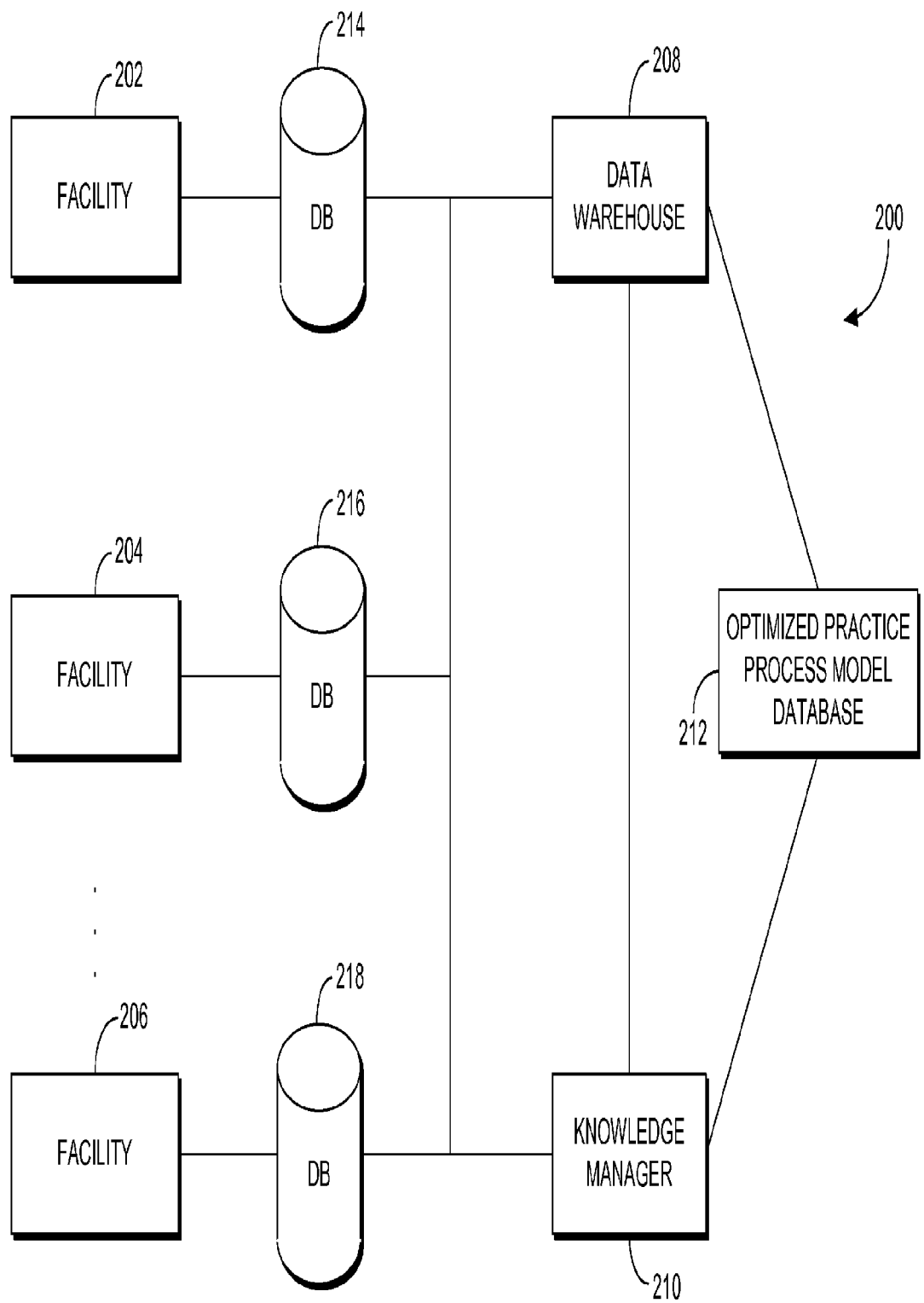
FIG. 2 is a block diagram showing an exemplary overall system architecture in which clinical system optimization may be performed in accordance with an embodiment of the present invention.
Figure 5:
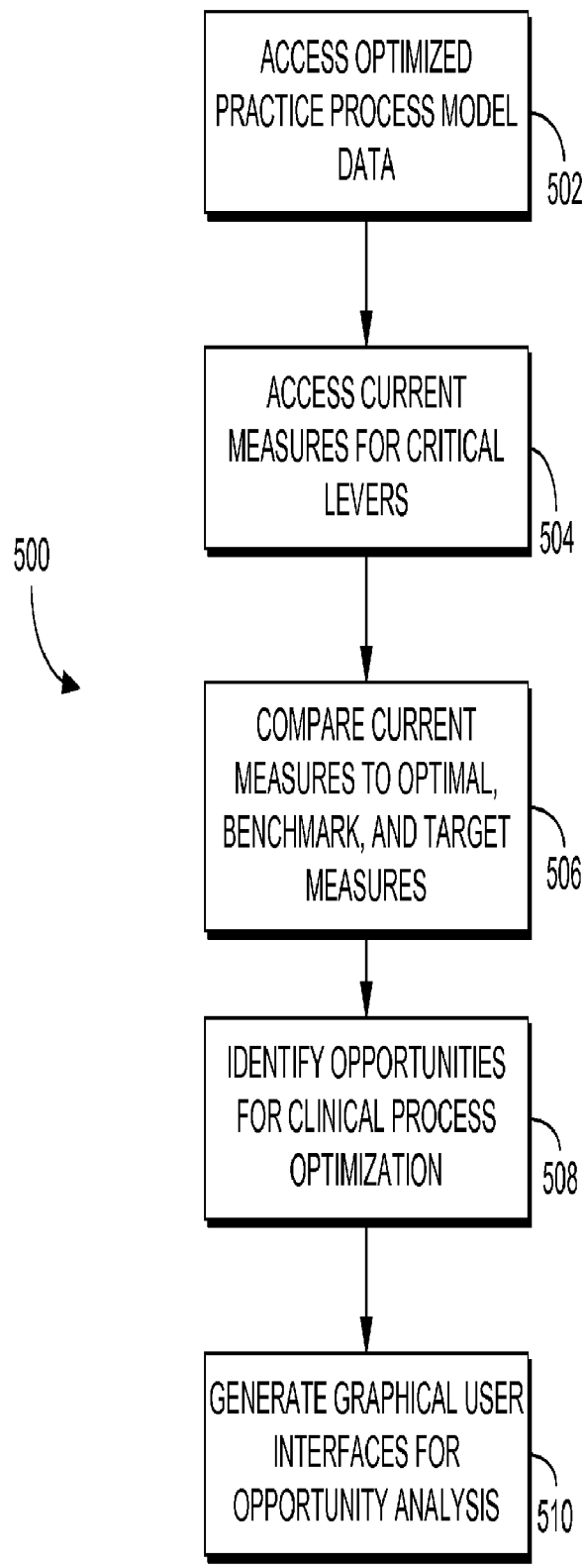
FIG. 5 is a flow diagram showing a method for identifying opportunities for clinical process optimization in accordance with an embodiment of the present invention.

Having described an exemplary computing system environment, an exemplary overall system architecture 200 in which embodiments of the present invention may be employed is shown in FIG. 2. The overall system architecture 200 may include a number of clinical facilities, such as the clinical facilities 202, 204, 206, a data warehouse 208, a knowledge manager 210, and an optimized practice process model database 212. The overall system architecture 200 shown in FIG. 2 is illustrative, and modifications in configuration and implementation will occur to persons skilled in the art. For instance, while the overall system architecture 200 is shown with only a single knowledge manager 210, in embodiments, multiple components may be employed independently or together to analyze opportunities for clinical process optimization within clinical facilities. Likewise, in various embodiments, more than one data warehouse and optimized practice process model database may be employed. Further, components shown separately within FIG. 2 may be combined in embodiments of the present invention.

The overall system architecture 200 shown in FIG. 2 provides a system that may be employed to identify and analyze opportunities or objectives to improve clinical processes within a clinical facility or set of clinical facilities (e.g., a collection of clinical facilities within a healthcare system). The opportunities often address health considerations within a clinical process. Opportunities for process optimization may be identified by comparing current measures from a current clinical process within a clinical facility against an optimized practice process model for the particular type of clinical process being analyzed.

The optimized practice process model database 212 may store one or more optimized practice process models, each of which contains data relating to an optimal clinical process. Each optimal clinical process details the activities required within the end-to-end process flow, including the actors and venues required to accomplish each activity. By defining an optimal clinical process, embodiments of the present invention recognize and account for interrelationships between activities within a process flow, thereby providing a significant advantage over other approaches in which individual pieces of evidence are used in isolation of an overall end-to-end process.

The optimal clinical process may be defined based on a variety of different data within the scope of the present invention. Typically, available literature and best published evidence (e.g., medical, clinical, operational, and other guidelines, trade magazines, and the like) may be used to define the optimal clinical process. In addition, operational evidence collected from a variety of facilities (such as that stored in the data warehouse 208 described in further detail below), may be used to define the optimal clinical process. One skilled in the art will recognize that a variety of other data may also be used within the scope of the present invention.

Within each optimal clinical process, activities that have the greatest impact on outcomes are identified as critical levers within the data. In other words, the critical levers represent those activities that present the greatest opportunities for optimizing the clinical process. An optimal measure is also identified for each critical lever and associated with each critical lever within the optimized practice process model database 212. Similar to defining the optimal clinical process, identification of the critical levers and an optimal measure for each critical lever may be based on best published evidence, available operational data, and other clinically-related data that may aid in the identification of best practices. Because the reliability of such information varies widely, the credibility of the source of information may also be included in the optimized practice process model.

Each critical lever or a set of critical levers may represent a potential opportunity for clinical process optimization. Accordingly, information related to the opportunity for clinical process improvement for each critical lever or set of critical levers may also be defined and stored within the optimized practice process model database 212. Generally, the critical levers may represent clinical, regulatory, operational, and/or financial opportunities. In addition, return-on-investment (or performance improvement) metrics may be defined within the optimized practice process model for determining a return-on-investment for implementing each opportunity to allow prioritization of opportunities. The return-on-investment metrics may include benefit metrics for determining a benefit for adopting an opportunity. The benefit metrics may include data to allow for the quantification of both financial and non-financial benefits of each opportunity. In addition, the return-on-investment metrics may include effort metrics for quantifying an effort for adopting each opportunity. Further, because the optimal clinical process within an optimized practice process model details the end-to-end activities of a particular clinical process, the models contain data regarding the changes necessary to adopt opportunities.

The optimized practice process model database 212 may be in communication with the knowledge manager 210, which may be employed to perform opportunity identification and analysis. The knowledge manager 210 may likewise be in communication with a source of data relating to one or more clinical facilities. In particular, the knowledge manager 210 may access a clinical facility's current measures for activities corresponding with critical levers defined by an optimized practice process model, and may compare those current measures with other defined measures, such as an optimal measure, a benchmark measure (based on measures from a collection of clinical facilities), and/or a target measure that has been defined for the clinical facility. The defined measures may be accessed from the optimized practice process model database, the data warehouse, and/or another associated database. Through the comparison, opportunities for process optimization for the clinical facility may be identified. The knowledge manager 210 further generates a number of graphical user interfaces to allow a user to analyze the identified opportunities and determine which opportunities to adopt and integrate into a current clinical process.

The knowledge manager 210 may access data regarding a clinical facility from the clinical facility itself or from a data warehouse, such as the data warehouse 208, which may store data from a number of different clinical facilities. Each clinical facility may be, for example, a hospital, clinic, research site, corporate facility, government or military site, or other facility that conducts medically-related operations. A clinical facility may have the ability to collect and condition captures of clinically-related data, including current measures for critical levers. In some cases, a database may be associated with a clinical facility for storing the clinically-related data, such as the databases 214, 216, and 218. Additionally, in some cases, a database may be associated with and store data for multiple clinical facilities. Each clinical facility may further communicate the clinically-related data to the knowledge manager 210 and/or the data warehouse 208. In addition to current measures for critical levers, the clinically-related data may include, for example, a variety of medical, financial, operational, administrative, and other information, including, for instance, sets of patient identification data, diagnosis data, patient morbidity, mortality and recovery rates, drug prescription and other drug delivery and management information, hospital or other occupancy data, revenue streams by department or facility, supply and capital cost information, medical staff information, scheduling information, or other types of information related to clinical operations.

The data warehouse 208 may collect and store clinically-related data, including current measures for critical levers, from multiple clinical facilities. The collection of data from multiple facilities may provide a number of advantages. For example, a benchmark measure for critical levers may be determined based on the provided data. Such benchmark measures may permit facilities to compare their performance against their peers. In addition, the collection of data may be used for various other analytic purposes. For example, if a particular facility is outperforming other facilities, its clinically-related data may be compared against its peers to determine why the facility is outperforming. Further, the collection of data may be used to improve the optimized practice process models. For example, the monitored data may indicate an optimal measure for a particular critical lever or suggest changes in the optimal clinical process.

Referring to FIG. 3, a flowchart is provided illustrating an exemplary overall process flow 300 for improving a current clinical process within one or more healthcare facilities in accordance with embodiments of the present invention. Generally, the overall method may be referred to as a closed-loop process that allows for the continuous improvement and refinement of clinical processes within clinical facilities. As shown at block 302, an optimized practice process model is defined for a particular type of clinical process. As discussed previously, an optimized practice process model contains data relating to what may be considered as an optimal procedure for a particular type of clinical process.

An exemplary method 400 for defining an optimized practice process model may be described with reference to FIG. 4. Initially, an optimal clinical process is determined for the particular type of treatment, as shown at block 402. As previously described, the optimal clinical process details the activities required within the end-to-end process flow, including the actors and venues required to accomplish each activity. Determination of the optimal clinical process may be based on a number of different sources. Typically, available literature and best published evidence (e.g., medical, clinical, operational, and other guidelines, trade magazines, and the like) may be used to define the optimal clinical process. In addition, operational evidence collected from a variety of facilities may be used to determine the optimal clinical process. After defining the optimal clinical process, the critical levers within that process are identified, as shown at block 404. The critical levers represent those activities within the process that, if varied, may have the greatest impact on outcomes.

A variety of data may be associated with each of the critical levers. For example, as shown at block 406, an optimal measure for each of the identified critical levers may be determined. The optimal measure may be based on best published evidence, available operational data, and other clinically-related data that may aid in the identification of best practices. Because the reliability of such information varies widely, the credibility of the source of information may also be included with the optimal measure for each critical lever.

Potential opportunities for clinical process improvement are next defined based on the critical levers, as shown at block 408. In some embodiments, each critical lever comprises a potential opportunity for clinical process improvement. In other embodiments, sets of critical levers define potential opportunities. Generally, each critical lever may be described as a clinical, financial, operational, and/or regulatory opportunity. In addition, data allowing for the quantification of the benefit and effort of each opportunity may be associated with each critical lever, as shown at block 410. This data allows each opportunity to be analyzed and prioritized based on both financial and non-financial considerations. The data may include return-on-investment metrics, including benefit metrics and effort metrics, for quantifying a return-on-investment to adopt an opportunity.

Referring again to FIG. 3, clinically-related data may be monitored and collected from a current clinical process within a clinical facility, as shown at block 304. In particular, the data monitored and collected includes current measures for activities corresponding with critical levers identified for the particular type of clinical process under review as defined within the optimized practice process model. Using the monitored data (in particular, the current measures associated with the critical levers) and the optimized practice process model for the particular clinical process, opportunities for process improvement may be identified, as shown at block 306. An exemplary method for identifying opportunities using a knowledge manager, such as the knowledge manager 210 of FIG. 2, may be described with reference to FIG. 5. As shown at block 502, the knowledge manager may access optimized practice process model data (e.g., from an optimized practice process model database, such as the optimized practice process model database 212 of FIG. 2) for the particular type of clinical process under review. In addition, the knowledge manager may access the clinical facility's current measures for the critical levers identified within the optimized practice process model, as shown at block 504. The knowledge manager may access the current measures, for example, from the clinical facility or from a common data warehouse, such as the data warehouse 208 of FIG. 2.

The current measures from the clinical facility may next be compared against an optimal measure, a benchmark measure, and/or a target measure, as shown at block 506. The optimal measure for a critical lever is the measure that is considered to be the ideal level for optimizing the clinical process. The benchmark measure represents the level at which other clinical facilities are operating (e.g., the average measure of other clinical facilities) to allow a clinical facility to determine how it is operating in comparison with its peers. The benchmark measure may be determined by accessing data contained within the data warehouse. In some embodiments, the benchmark measure may be based on data from all available clinical facilities. In other embodiments, the benchmark measure may be based only on a subset of the clinical facilities providing data. For example, a clinical facility may wish to compare its current measures against only similarly situated clinical facilities (e.g., based on size, type, region, etc.). Finally, the target measure for a critical lever represents a goal level that has been set for the clinical facility. For instance, because the optimal measure and/or benchmark measure may be difficult for a clinical facility to obtain, the facility may wish to set a goal for analyzing opportunities for improvement as well as monitoring its progress.

Based on the comparison of the current measure for the clinical facility against an optimal measure, benchmark measure, and/or target measure for each critical lever, the knowledge manager may identify opportunities for clinical process optimization, as shown at block 508. Essentially, through the comparison, the knowledge manager may identify which potential opportunities within the optimized practice process model data present areas of opportunity to improve the current clinical process within the healthcare facility. To provide for the analysis of the identified opportunities, the knowledge manager may also generate a number of graphical user interfaces, as shown at block 510. The graphical user interfaces may be generated using data from the optimized practice process model for the clinical process under review, including data, such as return-on-investment metrics, allowing for the quantification of the benefits and efforts associated with each opportunity.

Turning back to FIG. 3, after identifying opportunities for process optimization, the various identified opportunities may be analyzed, as shown at block 308. As mentioned above, the knowledge manager may provide a number of graphical user interfaces that a user may navigate to examine the various opportunities. The interfaces may allow the user to view the identified opportunities, as well as a variety of different aspects of the opportunities, for example, the activities/critical levers with which the opportunities are associated and their location within the optimal clinical process flow, the various measures for the critical levers (e.g., the current measure, optimal measure, benchmark measure, and/or the target measure), the type of opportunity (clinical, financial, operational and/or regulatory), the financial benefits of the opportunities, and the return-on-investment for the opportunities.

Using the graphical user interfaces provided by the knowledge manager, a user may prioritize the various opportunities and determine which opportunities to adopt. Based on that determination, the selected opportunities may be adopted and integrated into the current clinical process for the clinical facility, as shown at block 310. Because the optimized practice process model includes detailed information regarding the optimal clinical process, the model provides information regarding how to integrate the opportunities (e.g., changes required, actors and venues involved, etc.)

As mentioned previously, embodiments of the present invention provide a closed-loop approach to continuously improve the clinical processes of clinical facilities. Accordingly, as illustrated in FIG. 3, the process typically does not end with the adoption of selected opportunities. Instead, the clinical facility's operations are continuously monitored, as shown by the return to block 304, to allow for the identification and evaluation of out-of-tolerance conditions, as well as identifying and analyzing further opportunities for process optimization by repeating the process described with reference to block 304 through 310. Typically, a clinical facility may have the resources or ability to adopt only a subset of all identified opportunities at a given time. Accordingly, the process of identifying, analyzing, and adopting opportunities may be continuously repeated as appropriate for the facility.

As further represented in FIG. 3, by continuously monitoring and collecting data from multiple facilities, as well as evaluating the actual success of adopted opportunities, the optimized practice process model may be refined, allowing for further clinical process optimization. For example, the collected data may be used to either confirm or contradict existing information (publication, guideline, empirical data, etc.) that was used to define a particular portion of the optimal clinical process and/or used to set an optimal measure for a critical lever. In addition, the collected data may be used to define portions of the model in which no information is currently available or may prompt further research and clinical trials. Further, if one clinical facility is determined to be outperforming its peers, the data may be evaluated to determine why the facility is outperforming, and the optimized practice process model may be accordingly refined based on that evaluation As discussed previously, the knowledge manager may identify opportunities to optimize a current clinical process within a healthcare facility based on an optimized practice process model and may generate graphical user interfaces to allow a user to analyze and prioritize those opportunities. FIG. 6 through FIG. 12 are illustrative of user interfaces for reviewing and analyzing opportunities for process optimization. Although the user interfaces shown in FIG. 6 though FIG. 12 show opportunities as sets of clinical levers, as noted previously, in some embodiments, each critical lever may represent an individual opportunity. Accordingly, in such embodiments, the user interfaces may likewise allow for the analysis of opportunities comprising individual critical levers. In addition, although the user interfaces shown in FIG. 6 through FIG. 12 include opportunities for a single clinical facility, in some embodiments, user interfaces may be provided allowing for the analysis of opportunities identified for multiple facilities.

Referring initially to FIG. 6, an illustrative screen display 600 is provided showing an opportunity summary view in accordance with an embodiment of the present invention. The opportunity summary view provides an overview of the areas of opportunity identified by the knowledge manager for the current clinical process under review. Generally, the summary view may display each of the potential opportunities defined by the optimized practice process model and an indication as to whether each potential opportunity was identified as presenting an area of opportunity to improve the current clinical process under review.

As shown in the screen display 600, the opportunities identified by the knowledge manager may be summarized according to area of analysis 602 and venue 604. An indicator icon is provided showing each as an area of opportunity 606, an area of possible opportunity 608, that the client is meeting the measure 610, or that not enough information is available 612. No indicator icon for a particular area in the summary view (e.g., the blank area under the "Quality Care" area of analysis for the "Ambulatory" venue) indicates that the particular area was not studied (e.g., some clinical processes may not involve one or more venues). The screen display 600 may also include a data area 614, which may display additional data regarding the summary view, such as an identification of the clinical facility, the time period for analysis, and the study group volume.

A financial benefits summary view, such as that shown in the screen display 700 of FIG. 7, may also be provided. As shown in FIG. 7, the financial benefits summary view indicates the financial benefit that may be realized if a general area of opportunity is adopted and integrated into the facility's current clinical process. The financial benefits for each opportunity may be calculated based on financial data provided in the optimized practice process model, as well as the comparison of current measures against optimal, benchmark, and/or target measures.

Further details regarding a general area of opportunity may be viewed by navigating to an opportunity metrics interface. In some embodiments, for instance, each general area of opportunity within the screen display 600 and the screen display 700 may have an embedded link to allow users to select an area and view details. For example, if a user were to select the indicator icon 616 for the "Safety/Risk Management" area of analysis under the "Ambulatory" venue, an interface, such as that shown in the screen display 800 of FIG. 8, may be presented to the user. The screen display 800 illustrates an opportunity metrics interface providing a variety of details regarding the "Safety/Risk Management—Ambulatory" area of opportunity 802. A user may also view details of other general areas of opportunities by using a drop down menu 804 provided within the interface.

Figure 8:
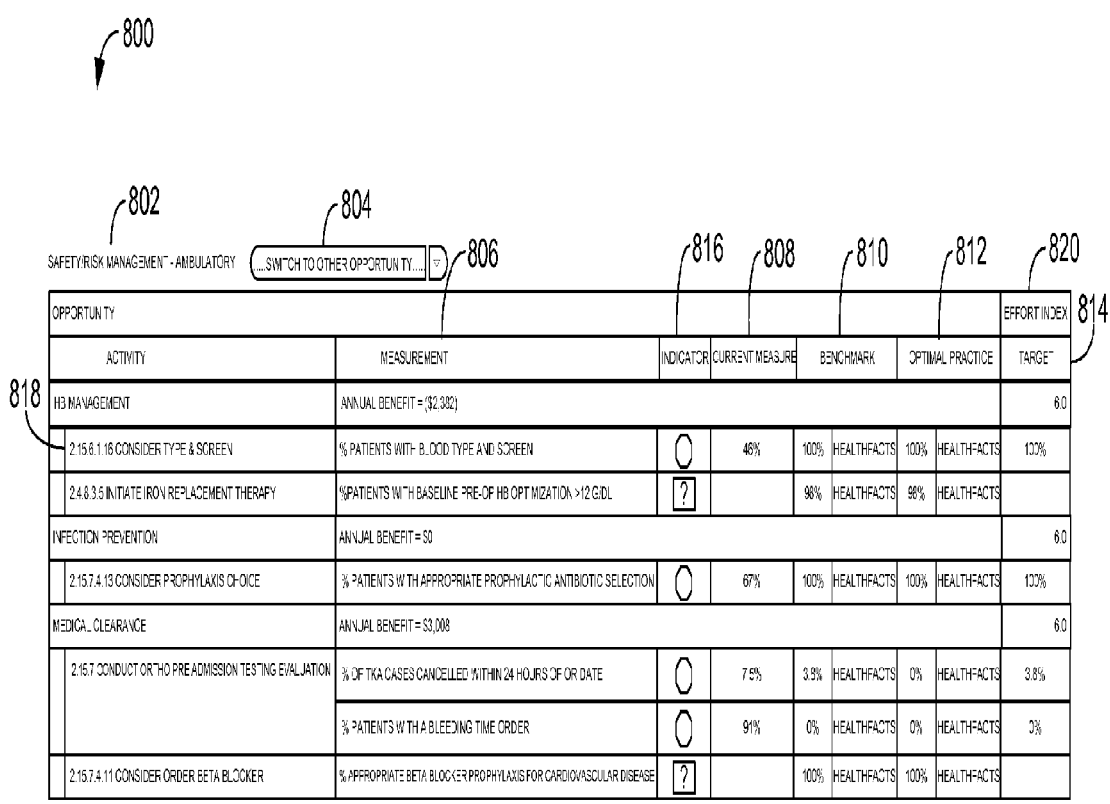
FIG. 8 is an illustrative screen display of an exemplary opportunity metrics user interface providing details regarding general areas of opportunity in accordance with an embodiment of the present invention.

Each general area of opportunity may have a number of activities from the optimal clinical process associated with it. These activities represent the critical levers for the particular area of opportunity being viewed. For example, as illustrated in FIG. 8, five activities have been associated with the "Safety/Risk Management—Ambulatory" area of opportunity 802. In addition, the activities may be grouped within the area of opportunity, such as the three groupings shown in the screen display 800: "Hb Management," "Infection Prevention," and "Medical Clearance."

For each activity, a description of the measurement 806 for the activity is provided, as well as the current measure 808, benchmark measure 810, optimal measure 812, and target measure 814 associated with that measurement. An indicator icon 816, similar to those used in the screen display 600 of FIG. 6, is also provided to indicate whether the particular activity presents an opportunity for process optimization. For example, for the activity labeled "2.15.6.1.16 Consider Type & Screen" 818, the measurement is the percentage of patients for which a blood type and screen is performed. As shown in FIG. 8, the clinical facility is currently performing a blood type and screen for only 46% of its patients, while the optimal, benchmark, and target measures are all 100%. Accordingly, the activity has been indicated as area of opportunity.

An effort index 820, representing a quantification of the effort to adopt an opportunity, may also be provided for the various opportunities to allow further analysis and prioritization as will be described in further detail below. As shown in the screen display 800, each grouping within the general area of opportunity has been assigned an effort index. In some embodiments, an effort index may be displayed for individual activities, while in other embodiments, an effort index may be displayed for the general area of opportunity. Each effort index may be determined based at least in part on effort metrics defined within the optimized practice process model.

An annual financial benefit may also be calculated for each opportunity and displayed to the user. In the screen display 800, for example, an annual financial benefit is shown for each grouping of activities. The financial benefit for each activity may be determined by comparing the current measure against one of the benchmark measure, the optimal measure, and the target measure for that activity and applying financial benefit metrics from the optimized practice process model. For example, a clinical facility may have a current measure for a particular activity of 75%, while the optimal measure is 100%. If the clinical facility handles 1000 cases annually and the cost benefit associated with the activity is $100 per case, the clinical facility may realize an annual benefit of $25,000 by achieving the optimal measure for the activity.

As discussed with respect to the effort index, in some embodiments, an annual financial benefit may be displayed for each activity, while in other embodiments, an annual financial benefit may also be displayed for the general area of opportunity. In addition, the financial benefit for each opportunity may be determined based at least in part on benefit metrics defined within the optimized practice process model. It should be noted that, as indicated for the "HB Management" grouping, an annual financial benefit may be a negative amount. This reflects that some opportunities may require changes that would cause the facility to incur additional costs, but the clinical, operational, and/or regulatory benefits may outweigh the financial cost. Additionally or alternatively, adoption of the opportunity may provide a benefit that is realized within one or more other activities within the clinical process flow justifying or offsetting the cost.

A user may also view the value of each activity within a general area of opportunity by navigating to an opportunity value interface. For example, the screen display 900 illustrated in FIG. 9 provides an opportunity value interface for the "Safety/Risk Management-Ambulatory" area of opportunity. The user interface indicates whether each activity represents a clinical opportunity 902, a regulatory opportunity 904, an operational opportunity 906, and/or a financial opportunity 908. For example, as shown in FIG. 9, the activity labeled "2.15.6.1.16 Consider Type & Screen" 910 presents a clinical, operational, and financial opportunity for process optimization.

Figure 10:
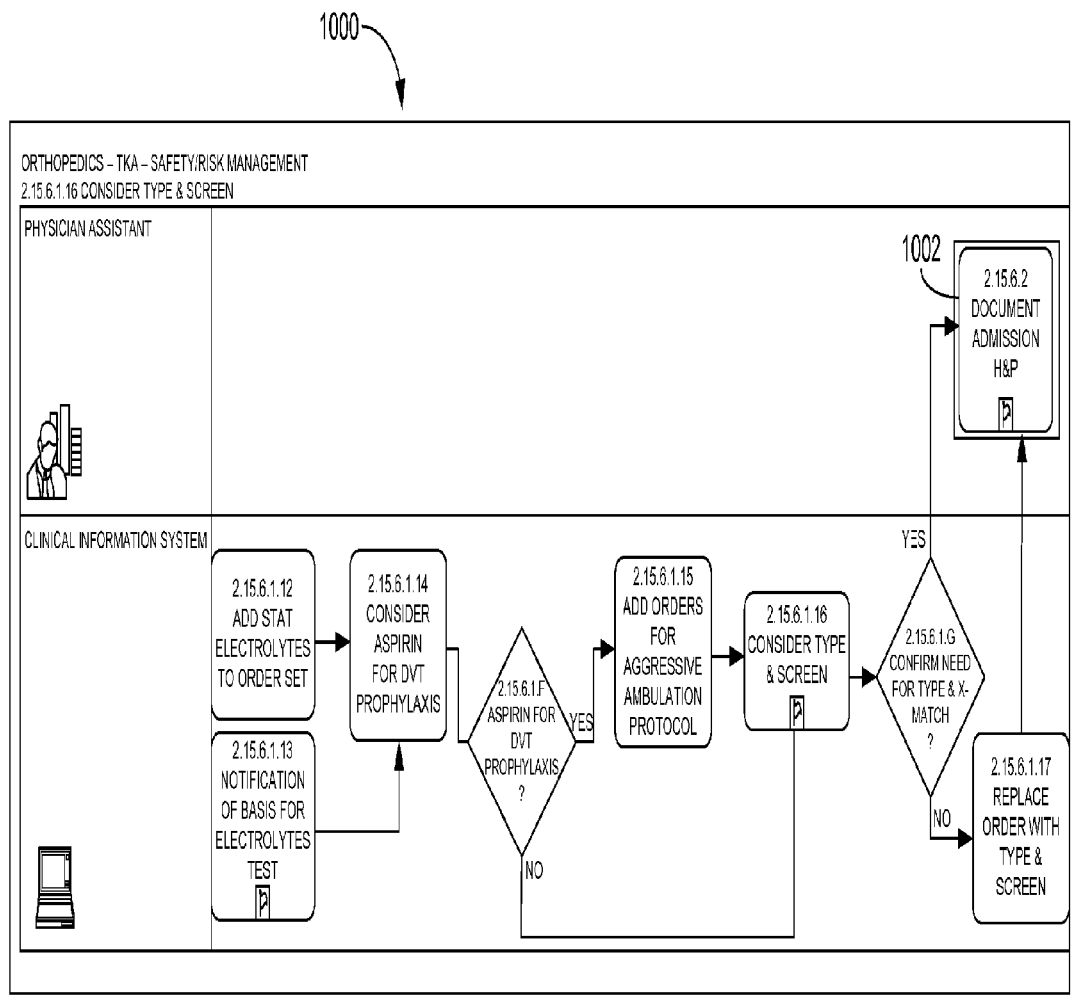
FIG. 10 is an illustrative screen display of an exemplary user interface for reviewing an optimal clinical process flow in accordance with an embodiment of the present invention.

A user may also wish to view the optimal clinical process and, more particularly, the location of a particular activity within that optimal process flow. Accordingly, the user may navigate to an interface for the optimal clinical process. In some embodiments, activities, such as those shown in either the screen display 800 of FIG. 8 or the screen display 900 of FIG. 9, may each have an embedded link to the optimal process flow that may be selected to view the process flow interface. For example, if a user were to select the activity labeled "2.15.6.1.16 Consider Type & Screen," the screen display 1000 shown in FIG. 10 may be presented to the user. As shown in FIG. 10, the embedded link may bring the user directly to the specific location of the selected activity 1002 within the optimal process flow. The user may then scroll through the optimal clinical process and view the various activities. In some embodiments, an indication, such as coloring of the activity or the display of a tag with the activity, for instance, may be provided to indicate those activities that have been designated as a critical lever and whether those activities have been identified as an area of opportunity or otherwise. Further, in some embodiments, each activity may have an embedded link that allows a user to navigate back to another interface, such as the opportunity metrics or value interfaces of FIGS. 9 and 10, for example.

Figure 11:
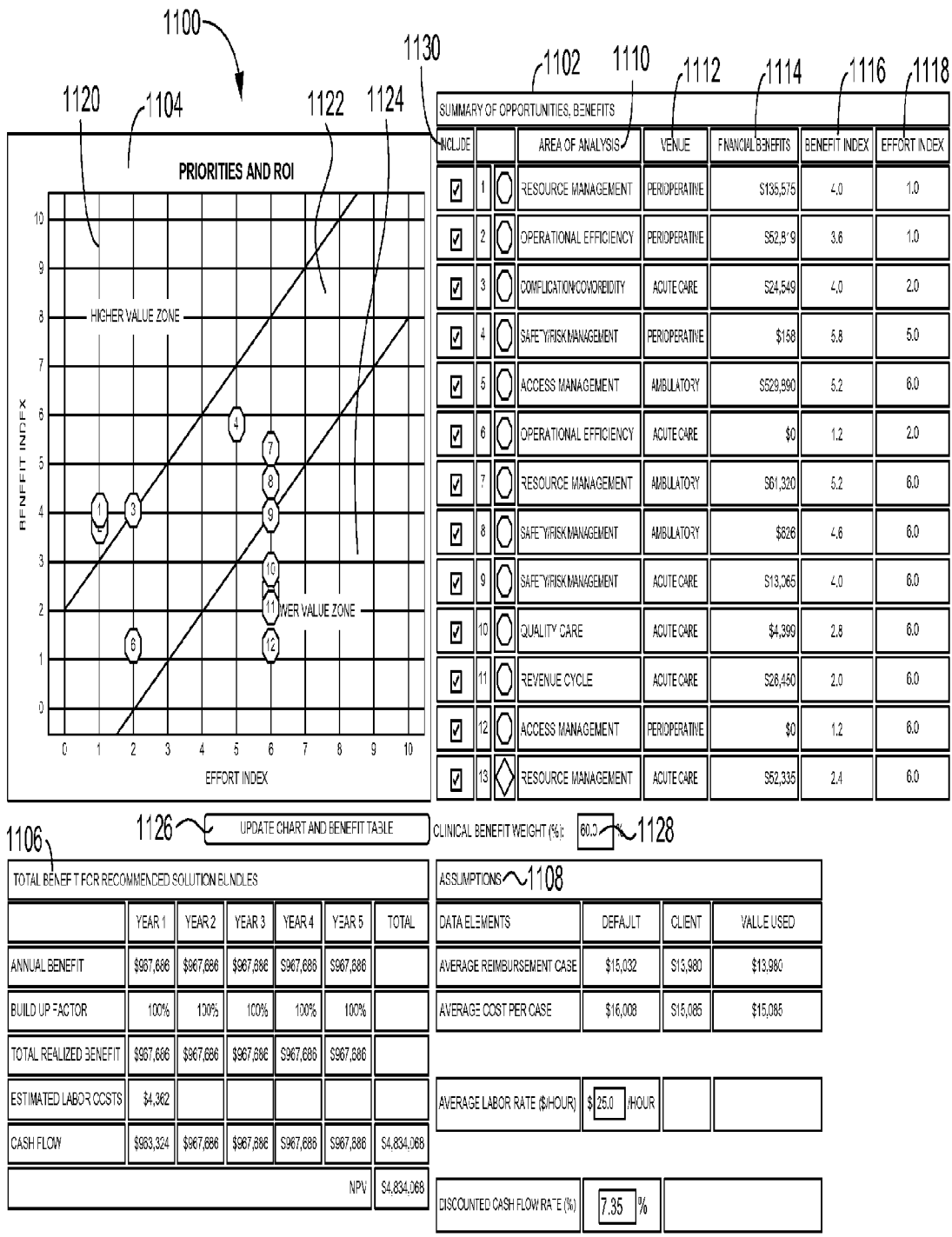
FIG. 11 is an illustrative screen display of an exemplary priority analysis user interface for prioritizing identified opportunities in accordance with an embodiment of the present invention, wherein all opportunities have been selected for analysis.
Figure 12:
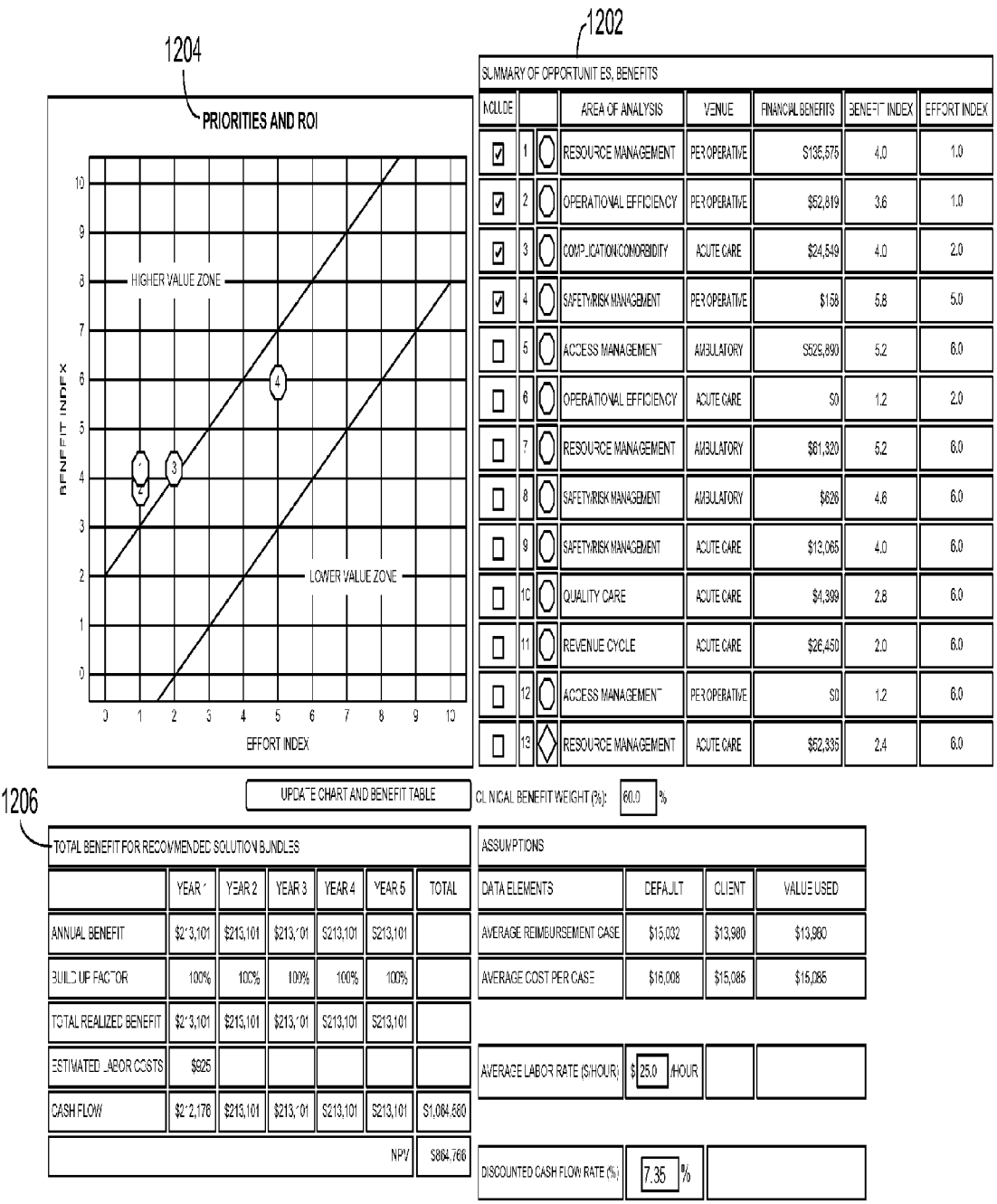
FIG. 12 is an illustrative screen display of an exemplary priority analysis user interface in accordance with an embodiment of the present invention, wherein only a subset of opportunities have been selected for analysis.
Figure 15:
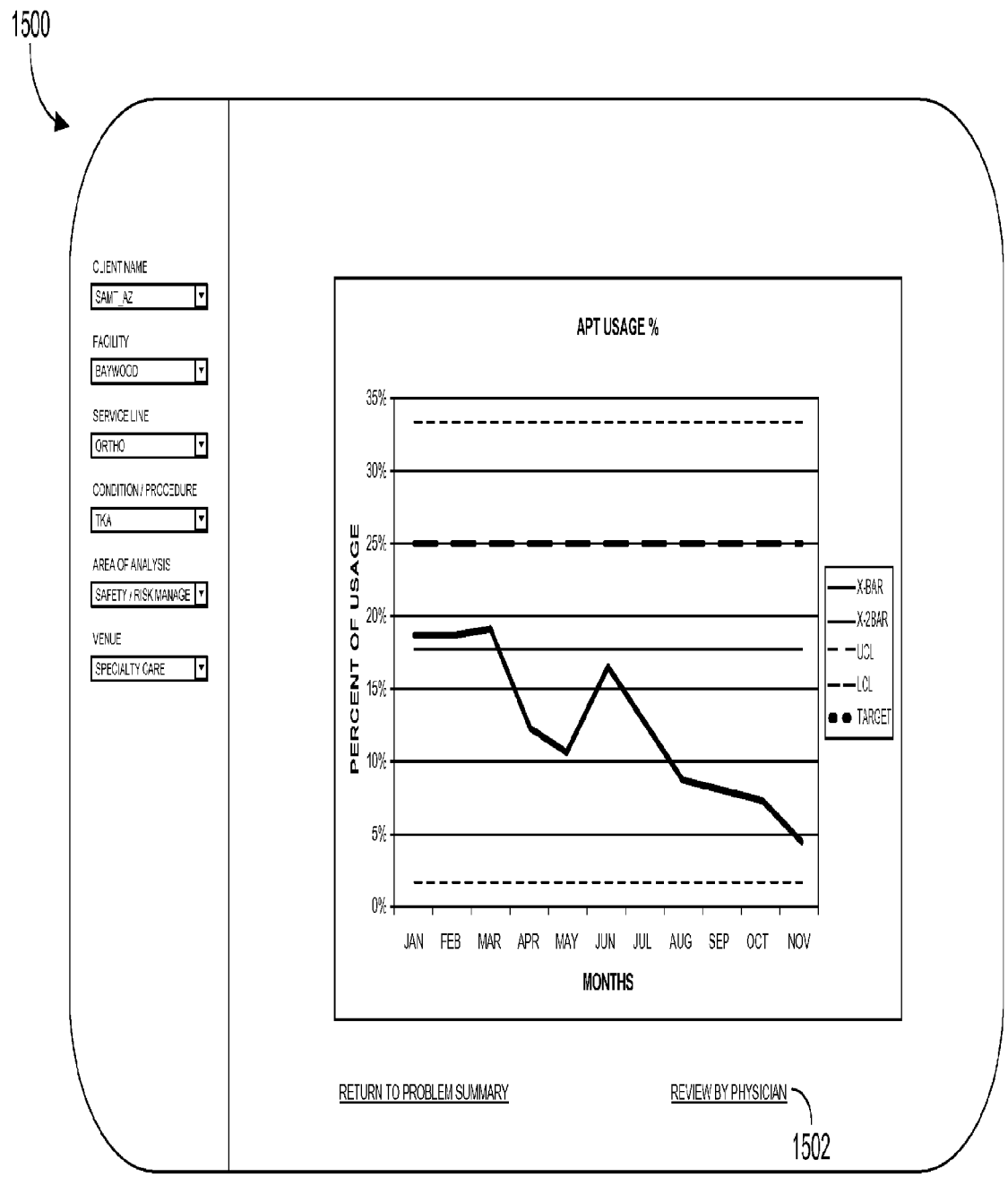
FIG. 15 is an illustrative screen display showing monitoring data relating to a rule violation indicated in the problem summary user interface in accordance with an embodiment of the present invention.

Referring now to FIG. 11, a screen display 1100 is provided showing a priority analysis user interface for further analyzing opportunities for process optimization. A user may employ the priority analysis user interface to evaluate the return-on-investment afforded by each opportunity identified by the knowledge manager and prioritize those opportunities for adoption. The return-on-investment for each opportunity may be based on return-on-investment metrics, including benefit metrics and effort metrics, defined within the optimized practice process model. As shown in FIG. 11, the priority analysis user interface may include a summary table 1102, a priorities chart 1104, a total benefit table 1106, and an assumptions area 1108.

The summary table 1102 lists the various opportunities that have been identified and provides summary information for each opportunity. Typically, the summary table 1102 will include those areas identified as either an area of opportunity or an area of possible opportunity, and an indicator icon may be provided for each. As shown in FIG. 11, the summary information may include an identification of each opportunity (e.g., the opportunities are identified by an associated "Area of Analysis" 1110 and "Venue" 1112), the financial benefits 1114, a benefit index 1116, and an effort index 1118. It should be noted that the information provided in the summary table 1102 is illustrative only and other information may be provided within the scope of the present invention.

The benefit index and effort index for each opportunity provide a convenient approach for comparing and prioritizing the opportunities. The benefit index quantifies the financial and non-financial benefits (e.g., clinical, financial, operational, and regulatory benefits) of each opportunity. The benefit index may be determined based on a weighted average of two factors. The first factor of the benefit index is based on the financial benefit of each opportunity, while the second factor is based on the "soft" benefits (e.g., clinical, operational, and regulatory benefits) that may present non-financial process improvements. To determine the financial factor of the benefit index, the opportunities are ranked based on financial benefits, and a relative value between zero and ten is assigned to each opportunity based on its rank. The soft benefits factor of the benefit index is based on subjective values assigned to each opportunity. These values may be pre-determined and defined within the optimized practice process model as the benefit metrics for each clinical process. The financial and non-financial factors may then be weighted and combined to determine the benefit index for each opportunity.

The effort index represents the ease or difficulty of changes required to adopt and integrate a particular opportunity into a facility's clinical process. It is a relative measure that is subjectively assigned to each opportunity. Similar to the measures for the non-financial benefits, the effort measures for each opportunity may be based on values that are pre-determined and defined within the optimized practice process model as effort metrics for each clinical process.

Opportunities may be displayed within the priorities chart 1104 based on their respective benefit index and effort index. Accordingly, the chart provides a visual representation of the return-on-investment for each opportunity, such that a user may readily identify those opportunities that will have the greatest impact on outcomes at the least amount of effort. Using the priorities chart, a user may prioritize the various opportunities and determine which opportunities to adopt.

As shown in FIG. 11 the priorities chart 1104 may be described as having three value zones: a higher value zone 1120, a middle value zone 1122, and a lower value zone 1124. Opportunities displayed in the higher value zone offer a greater value as they provide the greatest benefit at the least amount of effort. Opportunities in middle and lower value zone have a lower relative value as they provide benefit at a greater relative effort. By viewing the priorities chart 1104, a user may be able to readily determine which opportunities to adopt. For example, a user may choose to adopt only those opportunities within the higher value zone.

The total financial benefits for the identified opportunities are summarized in the total benefit table 1106. As shown in the screen display 1100 of FIG. 11, the total benefit table 1106 may include a variety of financial information to aid a user in determining the present and future value of adopting the opportunities.

The assumptions area 1108 of the priority analysis user interface details a variety of assumptions used in the process. For example, the assumptions area 1008 shown in FIG. 11 provides information relating to a number of assumptions, including the "Average Reimbursement per case," "Average Cost per case," "Average labor rate," and "Discounted Cash Flow Rate." In some embodiments, the assumptions may be user-adjusted by changing a value within the priority analysis user interface and clicking on an update button 1126. It should be noted that the assumptions shown in the screen display 1100 are illustrative only, and a variety of additional assumptions may be provided within the scope of the present invention.

In some embodiments of the present invention, the weighting applied to the financial and non-financial factors within the benefit index may also be user-adjusted. For example, the priority analysis user interface shown in the screen display 1100 provides a weighting input portion 1128 that allows a user to adjust the "Clinical Benefit Weight" (i.e. the weighting for the non-financial, soft benefits). After inputting a desired value in the weighting input portion 1128, the user may click on the update button 1126 to update the benefit indices and the corresponding location of the opportunities within the priorities chart 1104. Accordingly, a user may adjust the financial and non-financial contributions to the benefit indices to further analyze the various opportunities depending upon user-preferred outcomes. For example, a user may be primarily interested in realizing financial benefits and may decrease the clinical benefit weight to determine the opportunities that have the greatest financial return on investment. Alternatively, a user may be primarily interested in non-financial benefits (e.g., clinical, operational, and regulatory benefits) and may increase the clinical benefit weight such that the benefit indices better reflect the importance of those soft benefits.

Further, in some embodiments of the present invention, the opportunities included in the priorities chart 1104 and used to determine the total benefit displayed in the total benefit table 1106 may be user-adjusted. For example, as shown in the screen display 1100, the user interface has an "Include" indication 1130 within the summary table 1102. By clicking on the box corresponding with a particular opportunity, a user may choose whether to include the opportunity. For instance, in the screen display 1100 of FIG. 11, all opportunities have been selected to be displayed in the priorities chart 1104 and used to calculate the total benefit. If a user wished to evaluate only a subset of the total opportunities, the user may unselect opportunities and click on the update button 1126. For example, the screen shot 1200 of FIG. 12 illustrates the priorities analysis user interface if only the first four opportunities have been selected in the opportunity summary table 1202. As shown in FIG. 12, only those four selected opportunities are displayed on the priorities chart 1202. In addition, the values within the total benefit table 1204 are updated to reflect only those four opportunities.

The priorities analysis user interface shown in FIGS. 11 and 12 may further include embedded links to other user interfaces. For example, each of the indicator icons displayed on the priorities chart 1104 and in the opportunities summary table 1102 may have an embedded link to a user interface providing more detailed information regarding the corresponding opportunity (e.g., the user interface shown in the screen display 800 of FIG. 8).

Although the screen displays 1100 and 1200 of FIG. 11 and FIG. 12, respectively, illustrate a priority analysis user interface in which general areas of opportunity comprising sets of critical levers are analyzed, in various embodiments of the present invention, the priority analysis user interface may be used to analyze opportunities at varying levels. For example, as indicated previously, in some embodiments, opportunities may be analyzed at the individual critical lever or activity level.

As described previously, because embodiments of the present invention provide a closed-loop process for continuously improving clinical processes, monitoring of data from clinical facilities typically continues after opportunities have been adopted. The continuous monitoring allows for further refinement of the clinical processes, as well as the determination of variance (i.e. out-of-tolerance) conditions. Accordingly, embodiments of the present invention also include systems, methods, and graphical user interfaces for reviewing monitoring data collected from clinical facilities. FIG. 13 through FIG. 18 are illustrative of user interfaces that may be employed to review the monitoring data. The user interfaces may allow a user to identify variance conditions and manage efforts to determine the root cause of the condition and to decide whether any attempts to correct the condition should be pursued.

Referring initially to FIG. 13, a screen shot 1300 of a user interface for reviewing net changes in operation is provided. As shown in FIG. 13, the user interface may include an action list 1302, a watch list 1304, and an improvement list 1306. The action list 1302 includes areas that are indicated as areas of opportunity, the watch list 1304 includes areas that are indicated as possible areas of opportunity, and the improvement list 1306 includes areas in which the measurement is currently being met. The user interface may also provide other summary information, such as the client name 1308, facility 1310, service line 1312, area of analysis 1314, indicator 1316, previous indicator 1318, date changed 1320, and the status 1322. The areas presented in the user interface may be filtered to focus on specific areas, for example, by using the drop down menus 1324 shown in the screen shot 1300.

Figure 14:
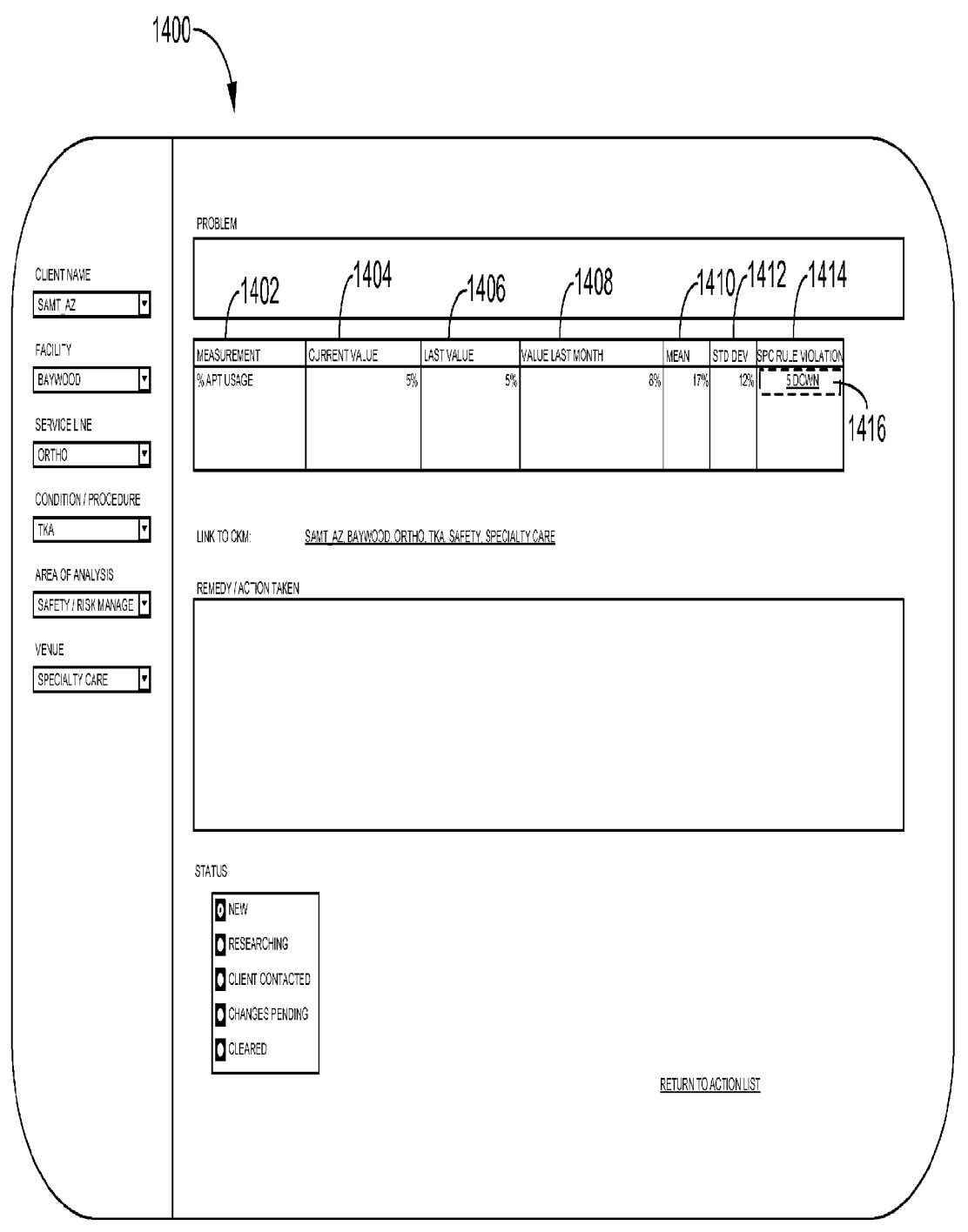

A succession of user interfaces may be provided to navigate various details of a particular area. For example, the screen shot 1400 of FIG. 14 illustrates an exemplary problem summary user interface for a selected area. The problem summary user interface may provide various summary information regarding variance conditions identified by the system. For example, the screen shot 1400 provides information including the measurement 1402 (i.e. % APT Usage) of interest, as well as a current value 1404, last value 1406, value last month 1408, mean 1410, and standard deviation 1412 for that measurement. In addition, a rule violation indication 1414 may be provided to indicate a rule that has been violated for the measurement. For example, the "5 Down" indication 1416 represents that there have been five consecutive declines in the value. As further illustrated in FIG. 14, the problem summary user interface may also be used to manage the condition. For example, a user may insert notes regarding the nature of the problem and any actions being taken to remedy the condition and may indicate the status of the selected area.

A user may view additional information regarding the rule violation to try to determine the root cause of the condition. For example, a user may select the rule violation in FIG. 14 (e.g., by clicking on the "5 Down" indication which may contain an embedded link), and the interface shown in the screen display 1500 of FIG. 15 may be provided. The screen display 1500 provides a chart indicating the facility's measure for APT usage percentage over the past year. By reviewing the chart, the user will readily recognize the decline in the measure.

Figure 16:
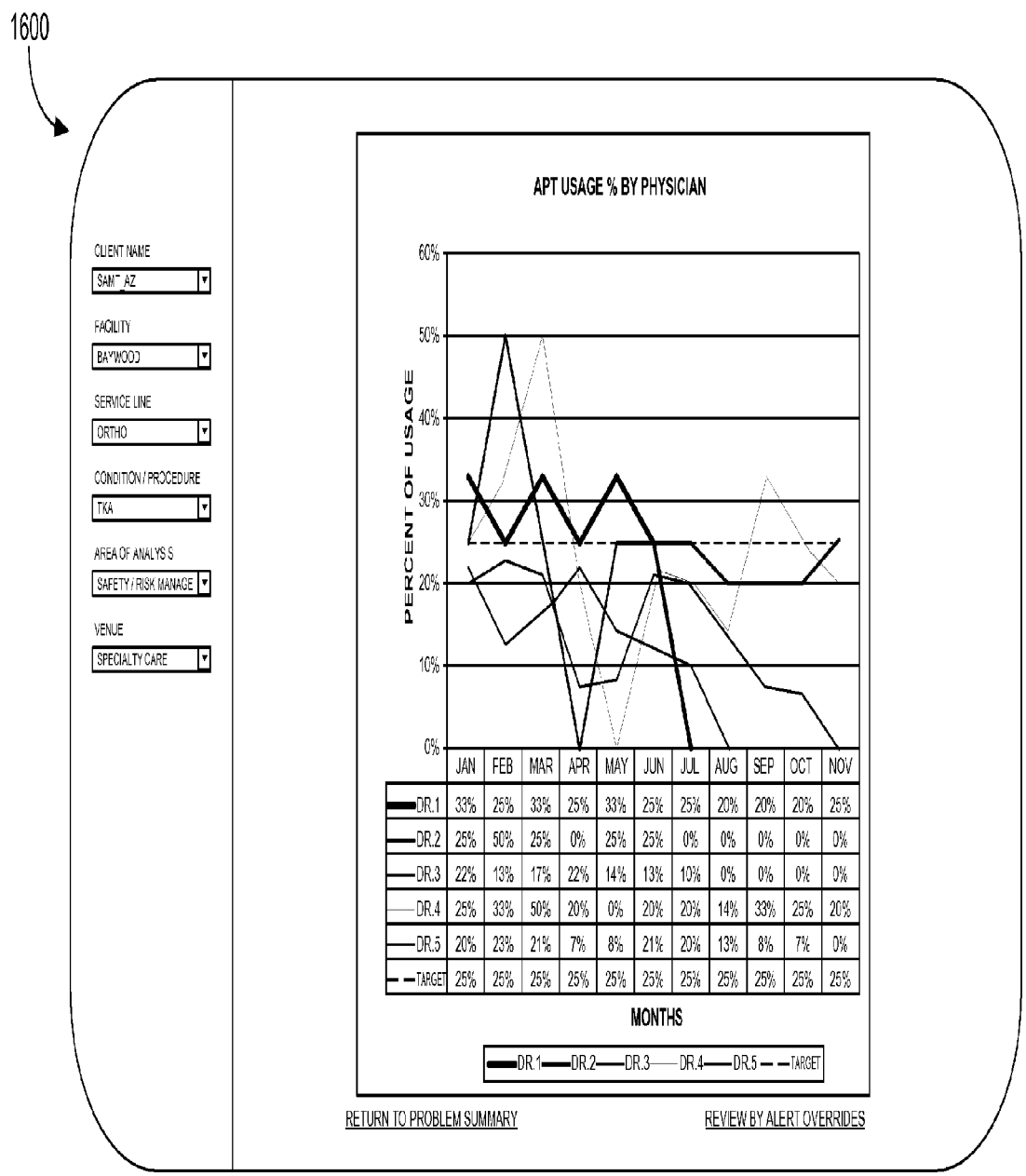
FIG. 16 is an illustrative screen display allowing review of the monitoring data by physician in accordance with an embodiment of the present invention.

By selecting the "Review by Physician" link 1502, the user may navigate to the user interface shown in the screen display 1600 of FIG. 16. As illustrated in FIG. 16, measures are provided at the individual physician level. Accordingly, the user may identify physicians who are deviating from optimal, benchmark, and/or target measures. With that knowledge, in some cases, the user may wish to contact the physicians to determine reasons for the deviations.

Figure 17:
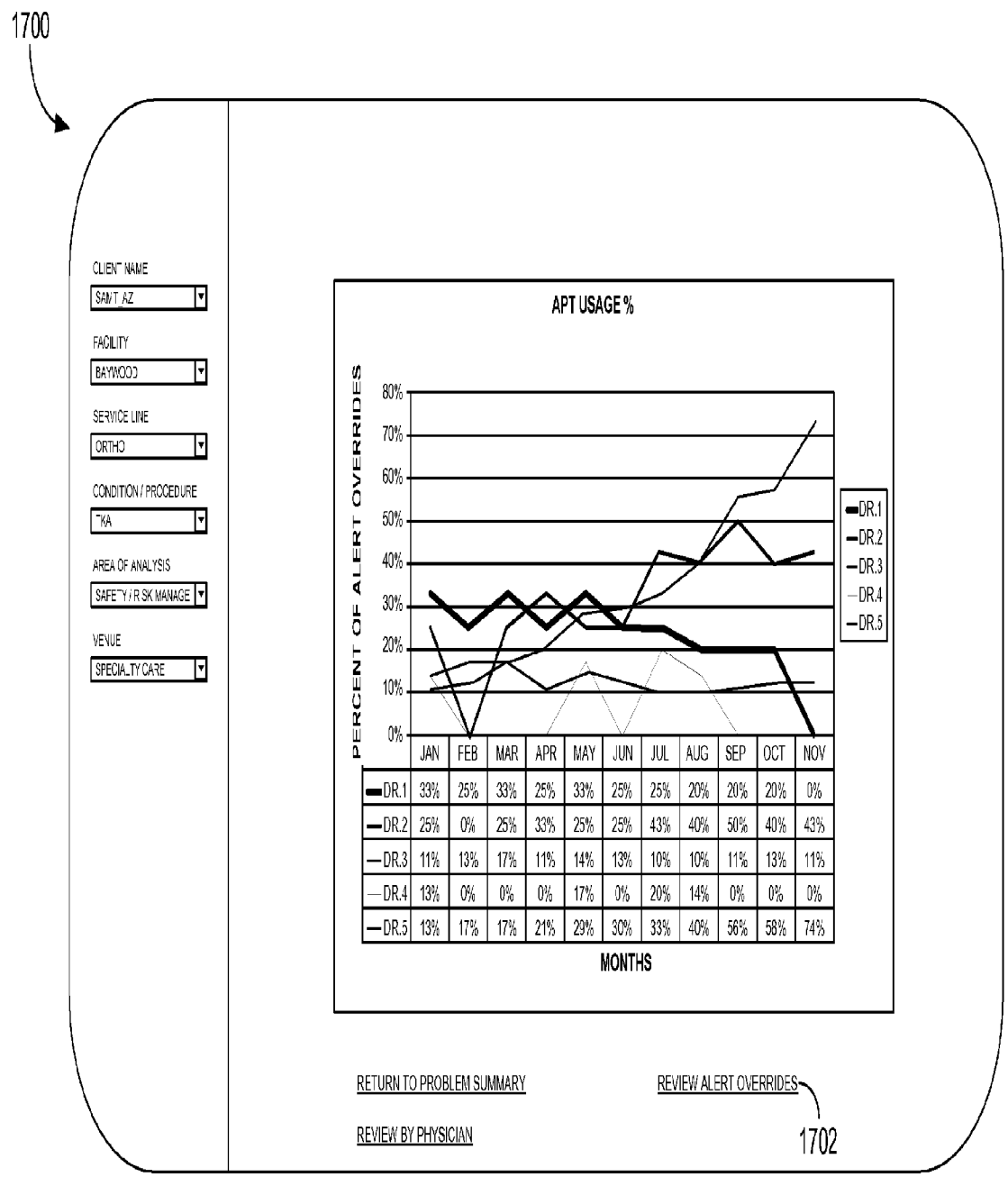
FIG. 17 is an illustrative screen display showing alert overrides in accordance with an embodiment of the present invention.
Figure 18:
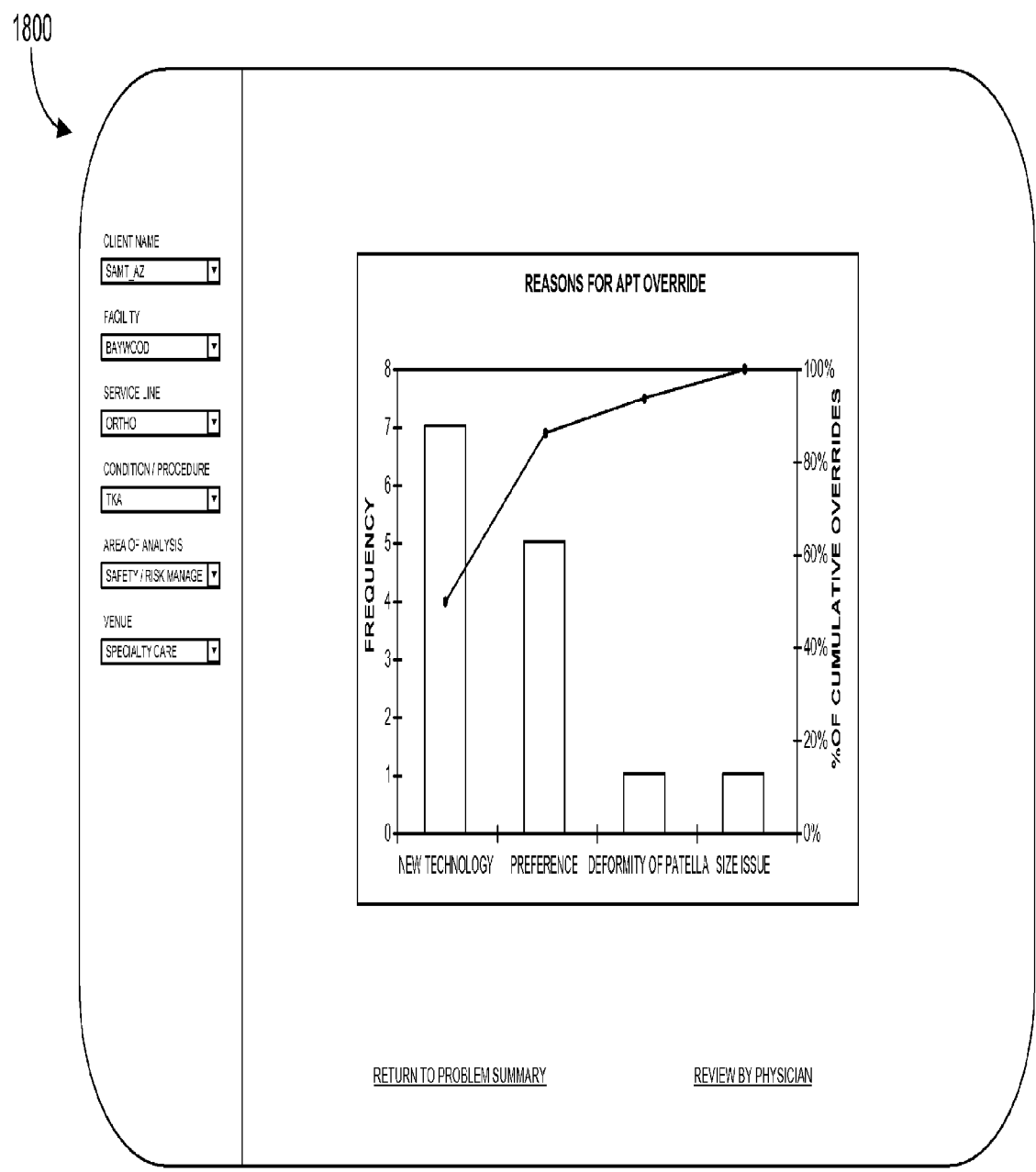
FIG. 18 is an illustrative screen display showing reasons for alert overrides in accordance with an embodiment of the present invention.

A user may also navigate to an alert overrides user interface, such as that shown in the screen display 1700 of FIG. 17. As shown in FIG. 17, the percent of alert overrides for the measurement may be provided at the individual physician level. A user may further review the alert overrides, for example, by selecting the "Review Alert Overrides" link 1702. As illustrated in the screen display 1800 of FIG. 18, the reasons for APT override may be provided. In reviewing the screen display 1800, the user may review the reasons provided for deviating from the measure and determine if any remedial action is required. In some cases, the deviations may require action to address the problem condition, while in other cases, the deviations may prompt a change in the optimal clinical process or defined measures for critical levers (e.g. the optimal and/or target measures).

Figure 19:
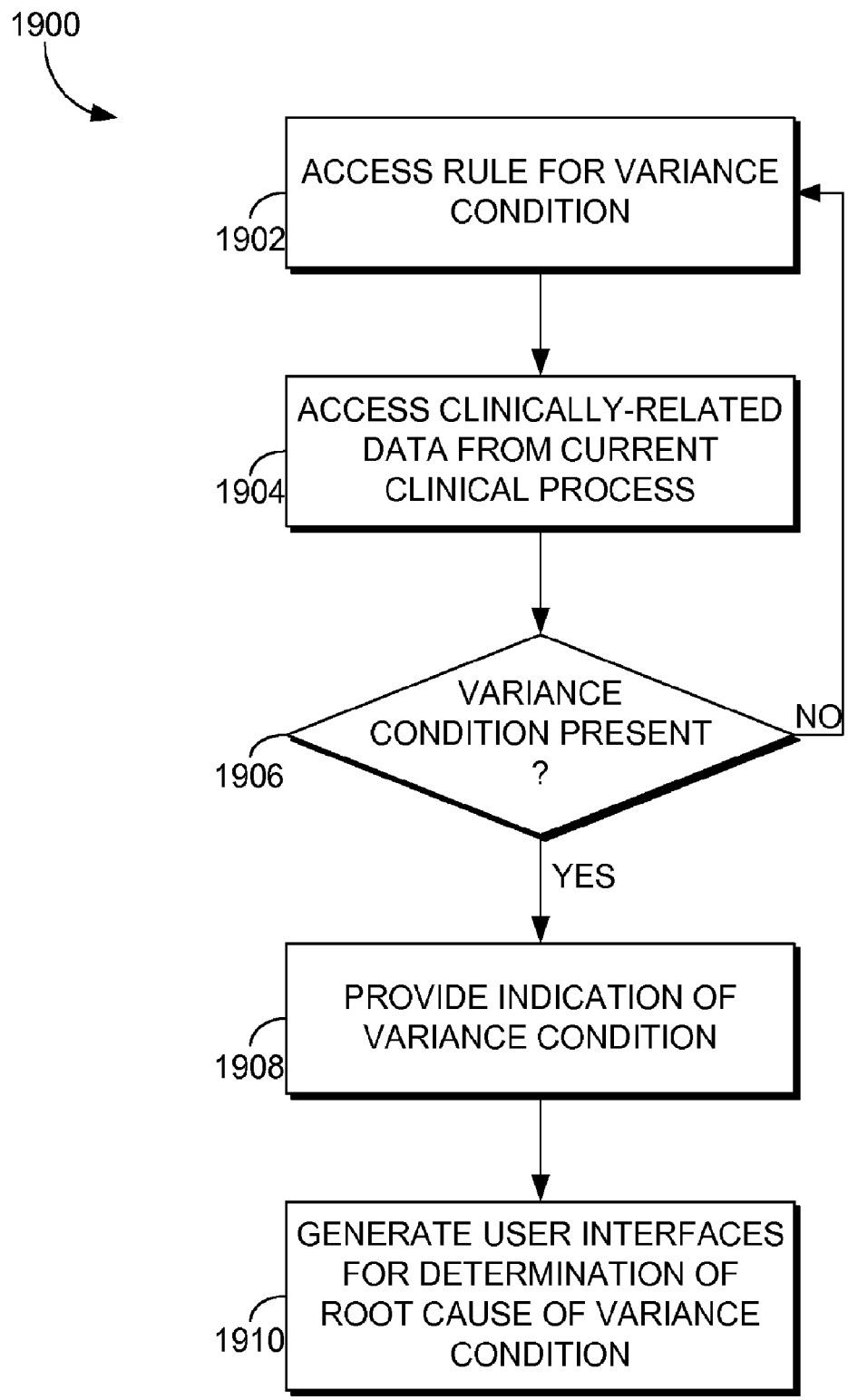
FIG. 19 is a flow diagram showing a method for monitoring a current clinical process for variance conditions in accordance with an embodiment of the present invention.

Referring now to FIG. 19, a flow diagram is provided illustrating an exemplary method 1900 for monitoring a current clinical process for variance conditions in accordance with an embodiment of the present invention. The process may begin at block 1902 when a knowledge manager accesses a rule for a variance condition. A variety of rules for variance conditions corresponding with critical levers and/or opportunities defined within an optimized practice process model may be used within embodiments of the present invention. By way of example only and not limitation, a rule for a variance condition may comprise a predetermined decline in a current measure over a period of time. In addition, a rule for a variance condition may comprise a predetermined difference between a current measure and one of an optimal measure, benchmark measure, and target measure. Generally, any number of rules may be defined for a particular clinical facility for monitoring its current clinical process for variance conditions.

Data required to determine if the variance condition is present is next obtained, as shown at block 1904. The knowledge manager may determine what data is required based on the rule previously accessed. Typically, the data will comprise one or more current measures for determining whether the particular variance condition being evaluated is present. The knowledge manager may access the clinically-related data from the clinical facility, from a data warehouse, or other associated database.

Comparing the accessed data against the rule for the variance condition, the knowledge manager may determine whether the variance condition is present, as shown at block 1906. The determination process is typically a continual process. Accordingly, if the variance condition is determined not to be present at block 1906, the determination process may be repeated, as represented by the return to block 1902. Alternatively, if the variance condition is determined at block 1906, an indication of the presence of the variance condition is provided, as shown at block 1908. In addition, user interfaces may be generated and provided to a user for the determination of a root cause of the variance condition. The user interfaces may utilize clinically-related data corresponding with the data used to determine whether the variance condition was present.

Further embodiments of the present invention may be employed to measure and evaluate performance improvements that have been realized for a clinical process. Performance improvements may be identified by comparing current measures for a particular clinical process against previous current measures, which operate as a baseline for purposes of improvement evaluation. For example, measures for critical levers for a clinical process for a first period of time may be set as the baseline. Current measures from a subsequent period of time may be compared against this baseline to measure the performance improvements that have been realized for the clinical process.

Figure 20:
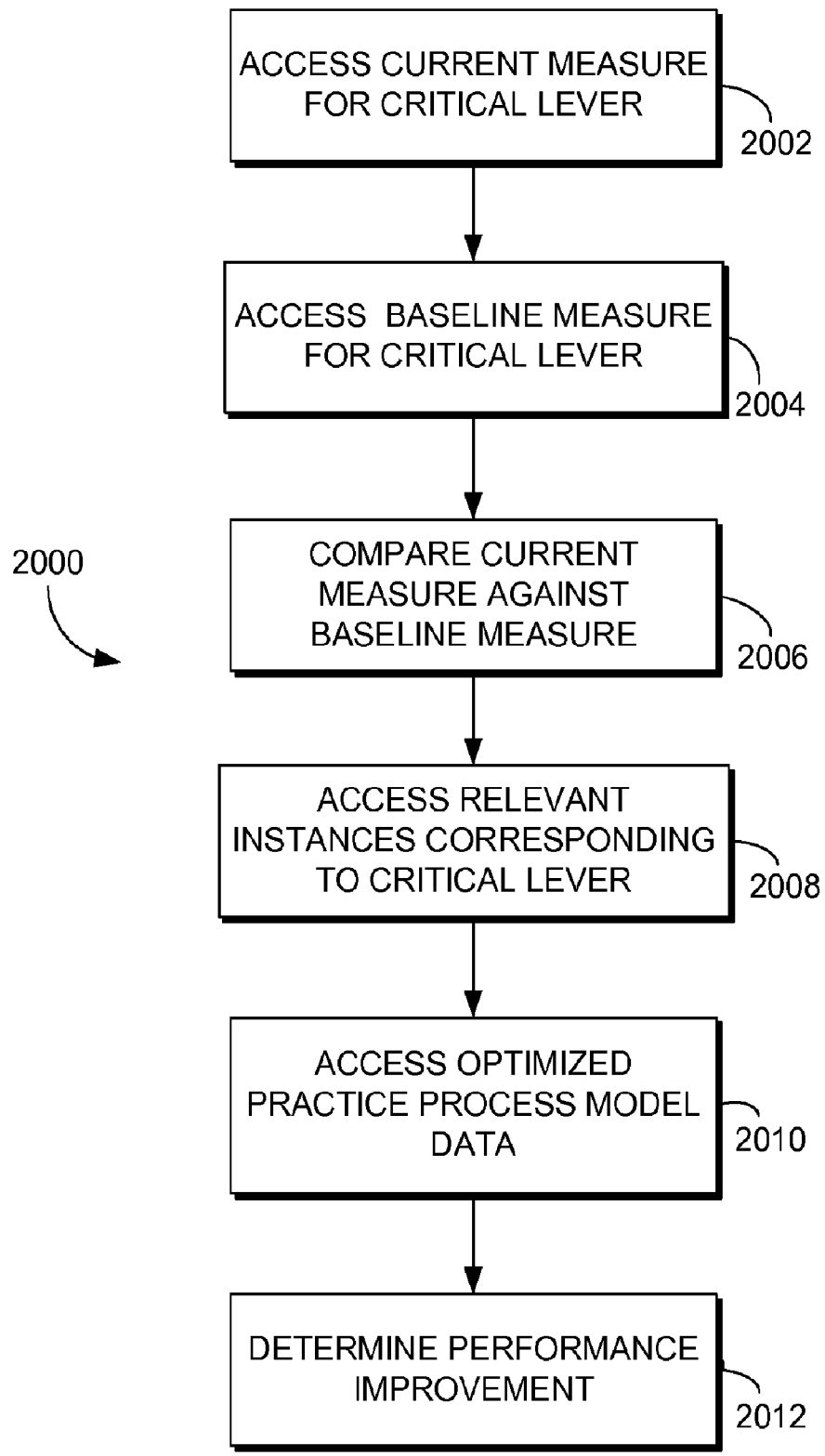
FIG. 20 is a flow diagram showing a method for measuring performance improvement for a clinical process within one or more healthcare facilities in accordance with an embodiment of the present invention.

Accordingly, referring to FIG. 20, a flow diagram is provided illustrating an exemplary method 2000 for measuring performance improvement for a clinical process within one or more healthcare facilities in accordance with an embodiment of the present invention. The process may begin at block 2002 when a knowledge manager accesses a current measure for a critical lever (i.e., an activity). At block 2004, the knowledge manager accesses a baseline measure for that particular critical lever. As indicated above, the baseline measure comprises a previous current measure for the critical lever. The current measure is compared against the baseline measure to determine a change in the critical lever, as shown at block 2006. The knowledge manager accesses those instances (e.g., number of cases or patients) corresponding with the critical lever, as shown at block 2008. Additionally, optimized practice process model data, such as benefit metrics, is accessed, as shown at block 2010. The performance improvement is then determined by applying the instances and the benefit metrics to the change in the critical lever, as shown at block 2012. In embodiments in which each opportunity comprises multiple critical levers, the performance improvement for an opportunity may be determined by aggregating the performance improvements determined for the critical levers comprising the opportunity.

An example of the determination of a performance improvement within a clinical process may be discussed with reference to FIG. 21, which illustrates an exemplary user interface 2100 showing performance improvements for a selected area of a clinical process. The determination of performance improvement is discussed herein with respect to financial benefits; however, in various embodiments of the present invention, performance improvement may be measured with respect to non-financial considerations, such as clinical, operational, and regulatory considerations, for example. As shown in FIG. 21, a current measure 2102 and baseline measure 2104 are indicated for each of the listed critical levers. In addition, the actual benefit (i.e. financial performance improvement) that has been realized for each of several opportunities is provided. For example, an actual benefit of $2500 is shown for "Medical Clearance." This benefit has been realized with respect to the measurement "% of TKA cases cancelled within 24 hours of OR date." As shown in FIG. 21, this measurement has decreased from a baseline measure of 7.5% to a current measure of 5%. Accordingly, if the number of cases for the clinical facility is 1000 cases, 25 fewer cases were cancelled within 24 hours of an OR date. If each case cancelled within 24 hours of an OR date creates a financial cost of $100 (a metric that may be defined within the optimized practice process model), the performance improvement has resulted in an actual benefit of $2500, as shown in FIG. 21.

As can be understood, the present invention provides systems, methods, and graphical user interfaces for identifying, analyzing, and adopting opportunities for clinical process optimization based on optimized practice process models. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. A computer-storage medium having stored thereon a data structure and computer code useable by a computing device for facilitating the analysis of a current clinical process within one or more clinical facilities, comprising:
  the data structure that includes:
    a first data field containing data representing a critical lever within an optimal clinical process for a type of clinical process corresponding with the current clinical process, the optimal clinical process having been predefined for the type of clinical process, the critical lever corresponding with an activity within the optimal clinical process that has been predetermined to have a greater potential to impact outcomes for the type of clinical process as compared to other activities in the optimal clinical process that have not been predetermined as critical levers;
    a second data field containing data representing an optimal measure for the critical lever;
    a third data field containing data representing benefit metrics that facilitate quantification of financial and non-financial benefits that may be realized by adopting changes to the current clinical process corresponding with the critical lever, wherein the benefit metrics are employed in conjunction with clinically-related data from the current clinical process to determine a benefit index associated with the critical lever;
    a fourth data field containing data representing effort metrics that facilitate quantification of financial and non-financial efforts required to adopt changes to the current clinical process corresponding with the critical lever, wherein the effort metrics are employed in conjunction with clinically-related data from the current clinical process to determine an effort index associated with the critical lever;

wherein the optimal clinical process, critical lever, optimal measure, benefit metrics, and effort metrics have been predefined based on at least one selected from the following: analysis of medical literature, published medical guidelines, and operational evidence collected from a plurality of clinical facilities; and the computer code including instructions to cause the computing device to employ the data structure to provide for prioritization of process improvement opportunities by: determining the benefit index for the critical lever based on the clinically-related data and the benefit metrics, determining the effort index for the critical lever based on the clinically-related data and the effort metrics, and calculating a return-on-investment for the critical lever as a function of the benefit index and effort index determined for the critical lever.

2. The computer-storage medium of claim 1, wherein the data structure further comprises a fifth data field containing data representing a benchmark measure for the critical lever.

3. The computer-storage medium of claim 1, wherein the data structure further comprises a fifth data field containing data representing a target measure for the critical lever.

* * * * *